(12) United States Patent
Ball

(10) Patent No.: US 12,109,120 B2
(45) Date of Patent: Oct. 8, 2024

(54) PRE-OPERATIVELY PLANNED HUMERAL IMPLANT AND PLANNING METHOD

(71) Applicant: STRYKER EUROPEAN OPERATIONS LIMITED, Carrigtwohill (IE)

(72) Inventor: Robert J. Ball, West Olive, MI (US)

(73) Assignee: STRYKER EUROPEAN OPERATIONS LIMITED, County Cork (IE)

( * ) Notice: Subject to any disclaimer, the term of this patent is extended or adjusted under 35 U.S.C. 154(b) by 574 days.

(21) Appl. No.: 17/215,242

(22) Filed: Mar. 29, 2021

(65) Prior Publication Data

US 2021/0212837 A1 Jul. 15, 2021

Related U.S. Application Data

(63) Continuation of application No. 16/164,555, filed on Oct. 18, 2018, now Pat. No. 10,987,226, which is a
(Continued)

(51) Int. Cl.
*A61F 2/40* (2006.01)
*A61B 34/10* (2016.01)
(Continued)

(52) U.S. Cl.
CPC ............ *A61F 2/4014* (2013.01); *A61B 34/10* (2016.02); *A61F 2/40* (2013.01); *A61F 2/4003* (2013.01);
(Continued)

(58) Field of Classification Search
CPC .. A61F 2/40; A61F 2/4014; A61F 2002/4011; A61F 2/4003; B33Y 80/00
See application file for complete search history.

(56) References Cited

U.S. PATENT DOCUMENTS

| 3,314,420 A | 4/1967 | Smith et al. |
| D243,286 S | 2/1977 | Deyerle |

(Continued)

FOREIGN PATENT DOCUMENTS

| CA | 211535 | 5/2022 |
| CA | 211538 | 5/2022 |

(Continued)

OTHER PUBLICATIONS

International Preliminary Report on Patentability issued in connection with International Patent Application No. PCT/US2022/070304, Sep. 28, 2023, 11 pages.
(Continued)

*Primary Examiner* — Jason-Dennis N Stewart
(74) *Attorney, Agent, or Firm* — DUANE MORRIS LLP

(57) ABSTRACT

Humeral prosthetic implants, systems, kits and methods of forming and using the humeral prosthetic implants, systems and kits are disclosed. The humeral prosthetic implants include proximal cup portions and distal stem portions, wherein the proximal cup portion is joined to the distal stem portion at a desired offset and/or angle configured based on an analysis of the humeral diaphysis and/or metaphysis offset in a patient. The humeral prosthetic implants may also include an adapter configured to join the proximal cup component with the stem component, wherein the adapter is configured to join the stem component to the stemless cup at a desired offset and/or angle.

13 Claims, 21 Drawing Sheets

Related U.S. Application Data continuation of application No. PCT/US2017/028470, filed on Apr. 19, 2017.

(60) Provisional application No. 62/324,372, filed on Apr. 19, 2016.

(51) Int. Cl.
    *B33Y 80/00*     (2015.01)
    *A61F 2/30*     (2006.01)
    *A61F 2/46*     (2006.01)

(52) U.S. Cl.
    CPC ..... *B33Y 80/00* (2014.12); *A61F 2002/30332* (2013.01); *A61F 2002/30477* (2013.01); *A61F 2002/30607* (2013.01); *A61F 2002/4022* (2013.01); *A61F 2002/4062* (2013.01); *A61F 2002/4668* (2013.01); *A61F 2310/00401* (2013.01); *A61F 2310/00407* (2013.01); *A61F 2310/00413* (2013.01)

(56) References Cited

U.S. PATENT DOCUMENTS

| | | |
|---|---|---|
| 4,310,931 A | 1/1982 | Muller |
| 5,108,451 A | 4/1992 | Forte |
| 5,324,293 A | 6/1994 | Rehmann |
| 5,665,118 A | 9/1997 | LaSalle et al. |
| 5,800,555 A | 9/1998 | Gray |
| 5,849,015 A | 12/1998 | Haywood et al. |
| 5,910,171 A | 6/1999 | Kummer et al. |
| 6,102,953 A | 8/2000 | Huebner |
| 6,165,224 A | 12/2000 | Tornier |
| 6,187,012 B1 | 2/2001 | Masini |
| 6,197,062 B1 | 3/2001 | Fenlin |
| D440,630 S | 4/2001 | Gottwald |
| 6,228,119 B1 | 5/2001 | Ondrla et al. |
| 6,283,999 B1 | 9/2001 | Rockwood, Jr. |
| 6,334,874 B1 | 1/2002 | Tornier et al. |
| 6,398,812 B1 | 6/2002 | Masini |
| 6,436,147 B1 | 8/2002 | Zweymuller |
| 6,468,314 B2 | 10/2002 | Schwartz et al. |
| 6,520,994 B2 | 2/2003 | Nogarin |
| 6,530,957 B1 | 3/2003 | Jack |
| 6,558,425 B2 | 5/2003 | Rockwood, Jr. |
| 6,648,894 B2 | 11/2003 | Abdelgany et al. |
| 6,673,114 B2 | 1/2004 | Hartdegen et al. |
| 6,679,916 B1 | 1/2004 | Frankle et al. |
| 6,702,854 B1 | 3/2004 | Cheal et al. |
| 6,719,799 B1 | 4/2004 | Kropf |
| 6,746,487 B2 | 6/2004 | Seifert et al. |
| 6,887,277 B2 | 5/2005 | Rauscher et al. |
| 6,899,736 B1 | 5/2005 | Rauscher et al. |
| 6,989,034 B2 | 1/2006 | Hammer |
| 7,001,389 B1 | 2/2006 | Navarro et al. |
| 7,011,686 B2 | 3/2006 | Ball et al. |
| 7,135,044 B2 | 11/2006 | Bassik |
| 7,166,132 B2 | 1/2007 | Callaway et al. |
| 7,175,663 B1 | 2/2007 | Stone |
| 7,309,360 B2 | 12/2007 | Tornier et al. |
| 7,445,638 B2 | 11/2008 | Benguin et al. |
| 7,758,650 B2 | 7/2010 | Dews et al. |
| 7,802,503 B2 | 9/2010 | Couvillion et al. |
| 7,998,217 B1 | 8/2011 | Brown |
| 8,231,684 B2 | 7/2012 | Mutchler et al. |
| 8,257,363 B2 | 9/2012 | Splieth et al. |
| 8,357,204 B2 | 1/2013 | Ragbir |
| 8,512,410 B2 | 8/2013 | Metcalfe et al. |
| 8,529,629 B2 | 9/2013 | Angibaud et al. |
| 8,545,504 B2 | 10/2013 | Durand-Allen et al. |
| 8,579,984 B2 | 11/2013 | Borowsky |
| 8,608,805 B2 | 12/2013 | Forrer et al. |
| 8,623,092 B2 | 1/2014 | Bickley et al. |
| 8,647,387 B2 | 2/2014 | Winslow |
| 8,663,333 B2 | 3/2014 | Metcalfe et al. |
| 8,663,334 B2 | 3/2014 | Viscardi et al. |
| 8,764,845 B2 | 7/2014 | Brooks et al. |
| 8,764,846 B2 | 7/2014 | Grappiolo |
| 8,888,855 B2 | 11/2014 | Roche et al. |
| 8,906,102 B2 | 12/2014 | Viscardi et al. |
| 8,945,234 B2 | 2/2015 | Humphrey |
| D744,612 S | 12/2015 | Peterson et al. |
| 9,283,075 B2 | 3/2016 | Wiley et al. |
| D757,252 S | 5/2016 | Von Moger et al. |
| 9,421,105 B2 | 8/2016 | Metcalfe et al. |
| 9,474,618 B2 | 10/2016 | Bickley et al. |
| 9,498,344 B2 | 11/2016 | Hodorek et al. |
| 9,566,162 B2 | 2/2017 | Isch |
| 9,597,190 B2 | 3/2017 | Chavarria et al. |
| 9,603,712 B2 | 3/2017 | Bachmaier |
| 9,610,165 B2 | 4/2017 | Poncet et al. |
| 9,622,869 B2 | 4/2017 | Nerot et al. |
| 9,700,423 B2 | 7/2017 | Stone et al. |
| 9,770,334 B2 | 9/2017 | Wiley et al. |
| 9,844,439 B2 | 12/2017 | Katrana et al. |
| 9,867,710 B2 | 1/2018 | Dalla Pria et al. |
| 9,925,047 B2 | 3/2018 | Klotz et al. |
| 9,956,083 B2 | 5/2018 | Humphrey |
| 10,034,759 B2 | 7/2018 | Deransart et al. |
| 10,143,558 B2 | 12/2018 | Frankie |
| 10,143,559 B2 | 12/2018 | Ries et al. |
| 10,172,714 B2 | 1/2019 | Hatzidakis et al. |
| 10,226,349 B2 | 3/2019 | Sperling et al. |
| 10,383,734 B2 | 8/2019 | Ekelund et al. |
| 10,433,967 B2 | 10/2019 | Deransart et al. |
| 10,548,737 B2 | 2/2020 | Hodorek et al. |
| 10,765,524 B2 | 9/2020 | Boileau et al. |
| 10,987,226 B2 | 4/2021 | Ball |
| 11,173,037 B2 | 11/2021 | Deransart et al. |
| D938,590 S | 12/2021 | Wolfe et al. |
| 11,229,522 B2 | 1/2022 | Nerot et al. |
| 2001/0010023 A1 | 7/2001 | Schwartz et al. |
| 2001/0011193 A1 | 8/2001 | Nogarin |
| 2001/0041940 A1 | 11/2001 | Pearl |
| 2002/0151982 A1 | 10/2002 | Masini |
| 2003/0028253 A1 | 2/2003 | Stone et al. |
| 2003/0097183 A1 | 5/2003 | Rauscher et al. |
| 2004/0002765 A1 | 1/2004 | Maroney et al. |
| 2004/0064190 A1 | 4/2004 | Ball et al. |
| 2004/0153161 A1 | 8/2004 | Stone et al. |
| 2004/0230311 A1 | 11/2004 | Cyprien et al. |
| 2005/0071014 A1 | 3/2005 | Barnett et al. |
| 2006/0020344 A1 | 1/2006 | Shultz et al. |
| 2006/0069445 A1 | 3/2006 | Ondrla et al. |
| 2006/0276905 A1 | 12/2006 | Calamel |
| 2007/0162140 A1 | 7/2007 | McDevitt |
| 2007/0173945 A1 | 7/2007 | Wiley et al. |
| 2007/0179624 A1 | 8/2007 | Stone et al. |
| 2007/0225726 A1 | 9/2007 | Dye et al. |
| 2007/0225821 A1 | 9/2007 | Reubelt et al. |
| 2007/0244562 A1 | 10/2007 | Roche et al. |
| 2007/0244565 A1 | 10/2007 | Stchur |
| 2008/0039860 A1 | 2/2008 | Trudeau |
| 2008/0183297 A1 | 7/2008 | Boileau et al. |
| 2008/0228281 A1 | 9/2008 | Forrer et al. |
| 2009/0182336 A1 | 7/2009 | Brenzel et al. |
| 2009/0210065 A1 | 8/2009 | Nerot et al. |
| 2009/0265010 A1 | 10/2009 | Angibaud et al. |
| 2009/0270865 A1 | 10/2009 | Poncet et al. |
| 2009/0281630 A1 | 11/2009 | Delince et al. |
| 2010/0049327 A1 | 2/2010 | Isch et al. |
| 2010/0076572 A1 | 3/2010 | Jamali |
| 2010/0094292 A1 | 4/2010 | Parrott |
| 2010/0114326 A1 | 5/2010 | Winslow et al. |
| 2010/0125336 A1* | 5/2010 | Johnson ............... A61F 2/4014 623/19.14 |
| 2010/0249797 A1 | 9/2010 | Trudeau et al. |
| 2010/0268232 A1 | 10/2010 | Betz et al. |
| 2010/0288421 A1 | 11/2010 | Kujawski et al. |
| 2011/0029089 A1 | 2/2011 | Giuliani et al. |
| 2011/0046625 A1 | 2/2011 | Boileau et al. |
| 2011/0060417 A1 | 3/2011 | Simmen et al. |
| 2011/0118846 A1 | 5/2011 | Katrana et al. |
| 2011/0125285 A1 | 5/2011 | Ragbir |

(56) References Cited

U.S. PATENT DOCUMENTS

| | | | |
|---|---|---|---|
| 2012/0143204 A1 | 6/2012 | Blaycock et al. | |
| 2012/0209394 A1* | 8/2012 | Bojarski | A61B 17/1764 |
| | | | 623/18.11 |
| 2012/0245646 A1 | 9/2012 | Gustilo et al. | |
| 2012/0253350 A1 | 10/2012 | Anthony et al. | |
| 2012/0253467 A1 | 10/2012 | Frankie | |
| 2013/0006369 A1 | 1/2013 | Wiley et al. | |
| 2013/0090736 A1 | 4/2013 | Katrana et al. | |
| 2013/0145609 A1* | 6/2013 | Sperling | A61F 2/30942 |
| | | | 29/592 |
| 2013/0197652 A1 | 8/2013 | Ekelund et al. | |
| 2013/0289738 A1 | 10/2013 | Humphrey | |
| 2013/0304228 A1 | 11/2013 | Phipps | |
| 2013/0325134 A1 | 12/2013 | Viscardi et al. | |
| 2014/0121709 A1 | 5/2014 | Gonzalez-Hernandez | |
| 2015/0190237 A1 | 7/2015 | Bonin, Jr. et al. | |
| 2015/0238324 A1 | 8/2015 | Nebosky et al. | |
| 2015/0245912 A1 | 9/2015 | Link | |
| 2015/0265411 A1 | 9/2015 | Deransart et al. | |
| 2016/0310176 A1 | 10/2016 | Van Dyke et al. | |
| 2016/0361173 A1 | 12/2016 | Reubelt et al. | |
| 2017/0043052 A1 | 2/2017 | San Antonio et al. | |
| 2017/0049573 A1 | 2/2017 | Hodorek et al. | |
| 2017/0056187 A1 | 3/2017 | Humphrey et al. | |
| 2017/0143494 A1* | 5/2017 | Mahfouz | A61F 2/34 |
| 2017/0273800 A1 | 9/2017 | Emerick et al. | |
| 2017/0304063 A1 | 10/2017 | Hatzidakis et al. | |
| 2017/0330449 A1 | 11/2017 | Deransart et al. | |
| 2018/0000598 A1 | 1/2018 | Amis et al. | |
| 2018/0280152 A1 | 10/2018 | Mutchler et al. | |
| 2018/0325687 A1 | 11/2018 | Deransart et al. | |
| 2018/0333265 A1 | 11/2018 | Termanini et al. | |
| 2019/0105169 A1 | 4/2019 | Sperling | |
| 2019/0231540 A1 | 8/2019 | Kim et al. | |
| 2019/0380839 A1 | 12/2019 | Deransart et al. | |
| 2020/0214847 A1 | 7/2020 | Hodorek et al. | |
| 2020/0289276 A1 | 9/2020 | Lefebvre et al. | |

FOREIGN PATENT DOCUMENTS

| | | |
|---|---|---|
| CN | 105213010 A | 1/2016 |
| CN | 209808650 U | 12/2018 |
| DE | 102 50 390 | 5/2004 |
| DE | 10 2005 003 097 | 7/2006 |
| DE | 102008010478 A1 | 8/2009 |
| EP | 0790044 A2 | 8/1997 |
| EP | 0898946 A1 | 3/1999 |
| EP | 0927548 A2 | 7/1999 |
| EP | 1093777 | 4/2001 |
| EP | 1402854 A2 | 3/2004 |
| EP | 1472999 A1 | 3/2004 |
| EP | 1415621 A2 | 5/2004 |
| EP | 1 520 562 | 4/2005 |
| EP | 1265555 | 11/2005 |
| EP | 1520560 B1 | 10/2006 |
| EP | 1952788 | 8/2008 |
| EP | 1048274 | 9/2012 |
| EP | 2 604 227 | 6/2013 |
| EP | 2604225 A1 | 6/2013 |
| FR | 2652498 A1 | 4/1991 |
| FR | 2 758 256 | 7/1998 |
| FR | 2773469 A1 | 7/1999 |
| FR | 2 932 678 | 12/2011 |
| FR | 3 025 089 | 3/2016 |
| GB | 1 504 055 | 3/1978 |
| JP | 2004-121850 | 4/2004 |
| JP | 2006-095300 | 4/2006 |
| JP | 2008528161 A | 7/2008 |
| JP | 2012143562 A | 8/2012 |
| WO | WO 93/09733 A1 | 5/1993 |
| WO | WO 96/17553 | 6/1996 |
| WO | WO 00/74554 | 12/2000 |
| WO | WO 2004/080331 | 9/2004 |
| WO | 2006079895 A1 | 8/2006 |
| WO | WO 2006/126238 | 11/2006 |
| WO | WO 2007/084939 | 7/2007 |
| WO | WO 2007/082925 | 10/2007 |
| WO | WO 2008/000928 A2 | 1/2008 |
| WO | WO 2008/050091 | 5/2008 |
| WO | 2008067400 A2 | 6/2008 |
| WO | WO 2008/109751 | 9/2008 |
| WO | WO 2013/064569 | 5/2013 |
| WO | 2014005644 A1 | 1/2014 |
| WO | WO 2014/067961 | 5/2014 |
| WO | WO 2014/178706 | 11/2014 |
| WO | WO 2015/112307 | 7/2015 |
| WO | WO 2016/094739 | 6/2016 |
| WO | WO 2017/184792 | 10/2017 |
| WO | WO 2019/053576 | 3/2019 |
| WO | WO 2019/106276 | 6/2019 |
| WO | WO 2019/106277 | 6/2019 |
| WO | WO 2019/178104 | 9/2019 |

OTHER PUBLICATIONS

Non-Final Office Action issued in connection with U.S. Appl. No. 17/149,527, Jan. 3, 2024, 17 pages.
First Office Action issued in connection with Japanese Patent Application No. 2022-183335, Aug. 15, 2023, 3 pages.
Non-Final Office Action issued in connection with U.S. Appl. No. 16/910,663, Jan. 16, 2024, 8 pages.
First Office Action issued in connection with Chinese Patent Application No. 201910099418.5, Feb. 7, 2024, 14 pages.
Non-Final Office Action issued in connection with U.S. Appl. No. 17/227,971, Feb. 16, 2024, 17 pages.
Extended European Search Report issued in connection with European Patent Application No. 23210681.5, Feb. 12, 2024, 9 pages.
Final Rejection issued in connection with U.S. Appl. No. 16/717,339, Oct. 13, 202, 28 pages.
International Search Report and Written Opinion issued in connection with International Patent Application No. PCT/US2022/070304, May 17, 2022, 15 pages.
Examination Report No. 1 for standard patent application from counterpart Australian Application No. 2017253113, dated May 10, 2021, 4 pp.
Response to Examination Report No. 1 for standard patent application from counterpart Australian Application No. 2017253113, dated May 10, 2021, filed Aug. 24, 2021, 66 pp.
Examination Report from counterpart European Application No. 17722238.7, dated Aug. 13, 2019, 5 pp.
Communication re Consultation from counterpart European Application No. 17722238.7, dated Oct. 4, 2019, 5 pp.
Response to Communication re Consultation from counterpart European Application No. 17722238.7, dated Oct. 4, 2019, filed Feb. 13, 2020, 54 pp.
Examination Report from counterpart European Application No. 17722238.7, dated Jul. 1, 2020, 4 pp.
Response to Examination Report from counterpart European Application No. 17722238.7, dated Jul. 1, 2020, filed Dec. 24, 2020, 47 pp.
Examination Report from counterpart European Application No. 17722238.7, dated Apr. 19, 2021, 5 pp.
Response to Examination Report from counterpart European Application No. 17722238.7, dated Apr. 19, 2021, filed Aug. 12, 2021, 55 pp.
International Preliminary Report on Patentability from International Application No. PCT/US2017/028470, dated Oct. 23, 2018, 9 pp.
Prosecution History from U.S. Appl. No. 16/164,555, dated Sep. 11, 2020 through Mar. 3, 2021, 21 pp.
Non-Final Office Action issued in connection with U.S. Appl. No. 17/590,234, May 20, 2022, 10 pages.
Communication issued in European Patent Application No. 18837131. 4, Jul. 13, 2022, 6 pages.
Notice of Acceptance from counterpart Australian Application No. 2017253113, dated Sep. 23, 2021, 3 pp.
First Examination Report issued in connection with Australian Patent Application No. 2020204546, Oct. 21, 2021, 9 pages.
First Office Action issued in connection with Japanese Patent

(56) References Cited

OTHER PUBLICATIONS

Application No. 2021-097158, Jun. 14, 2022, 4 pages.
Non-Final Office Action issued in connection with U.S. Appl. No. 16/717,339, Jul. 18, 2022, 15 pages.
International Search Report and Written Opinion issued in PCT Application No. PCT/US2017/028470, dated Aug. 7, 2017, in 14 pages.
Aston® Medical, "Operative Technique—Duocentric Expert Reversed, Total Shoulder Prosthesis".
Biomet Orthopedics, "Comprehensive® Shoulder System, Surgical Technique", 2007.
Delta, Delta CTA Reverse Shoulder Prosthesis, Surgical Technique, DePuy a Johnson & Johnson company, 2004.
Depuy, "GlobalTM Fx Shoulder Fracture System, Surgical Technique", 1999.
Depuy Synthes, "Global® UNITE Platform Shoulder System, Product Rationale & Surgical Technique", 2013.
DJO Surgical, "DJO Surgical Shoulder Solutions—Reaching Higher by Design", 2013.
Exactech, "Equinoxe Platform Shoulder System", 2014.
FH Orthopedics, "Arrow, Prothese d'epaule Universelle (Universal shoulder prosthesis)", Nov. 2009.
Integra, TitanTM Reverse Shoulder System, Surgical Technique, 2013.
JRI Orthopaedics, "Vaios® Shoulder System", 2011.
Levy et al., "Reverse Shoulder Prosthesis for Acute Four-Part Fracture: Tuberosity Fixation Using a Horseshoe Graft", J Orthop Trauma, vol. 25, No. 5, May 2011.
Lima Corporate, "Smr System, Surgical Technique".
Mathys European Orthopaedics, "Affinis® Fracture Affinis® Fracture Inverse, Technique operatoire".
Stryker Orthopaedics, "ReUnion Fracture System Surgical Protocol", 2007.
Tornier, "Aequalis Ascend Flex Convertible Shoulder System", Feb. 8, 2016.
Tornier, "Aequalis-Fracture Shoulder Prosthesis".
Tornier, "Aequalis ® Reversed Adapter, Surgical Technique Shoulder Revision System".
Tornier, "Aequalis® Reversed Fracture, Surgical Teachnique Reversed Shoulder Prosthesis".
Zimmer, "Anatomical ShoulderTM Fracture System, Surgical Technique", 2010.
Zimmer®, "Trabecular MetalTM Humeral Stem—Enabling fracture healing", 2009.
Extended European Search Report issued in connection with European Patent Application No. 23214740.9, 7 pages, Apr. 29, 2024.
Office Action issued in connection with Korean Patent Application No. 10-2021-7004528, May 6, 2021, 16 pages.
Med Gadget, "Tornier Announces First Implant in U.S. Trial of Its Simpliciti Stemless Shoulder Joint Replacement System", first available Aug. 5, 2011. (https:/Avwww.medgadget.com/2011/08/torier-announces-first-implant-in-u-s-trial-of-its-simpliciti-stemless-shoulder-joint-replacement-system.html) (Year: 2011), 1 page.
Wright Media, "Tornier Aequalis Reversed FX", first available May 19, 2016. (https:/Awww.wrightemedia.com/ProductFiles/Files/PDFs/ CAW-1146_EN_LR_LE.pdf) (Year: 2016), 6 pages.
Arthrex, "Univers Revers Shoulder Joint System", first available Apr. 24, 2019. (https:/Avww.arthrex.com/resources/surgical-technique-guide/ qkv6M00_50qt2QFBx1PKnA/univers-revers-shoulder-system) (Year: 2019).

\* cited by examiner

PRE-OPERATIVELY PLANNED HUMERAL IMPLANT AND PLANNING METHOD

CROSS REFERENCE TO RELATED APPLICATION

This application is a continuation of U.S. patent application Ser. No. 16/164,555, filed Oct. 18, 2018, which is a continuation of International Patent Application No. PCT/US2017/028470, filed Apr. 19, 2017, which claims priority benefit under 35 U.S.C. § 119(e) of U.S. provisional patent application No. 62/324,372 filed Apr. 19, 2016, the contents of each of which is incorporated herein by reference in its entirety.

FIELD OF THE INVENTION

The present invention relates generally to general surgery and orthopaedic implants for replacing an articulation surface in a joint. More specifically, but not exclusively, the present invention relates to implants and methods for shoulder replacement surgery.

BACKGROUND OF THE INVENTION

Shoulder replacement is a common surgical operation that has achieved positive results for many patients. Indeed, approximately 10% of joint replacement procedures globally are related to the shoulder. Many shoulder procedures are performed in a patient where substantial normal bone exists for orientation and fixation of a prosthetic replacement, or resurfacing. In these cases, the need for the shoulder replacement can often times be related mostly to the arthritic condition of the joint, and relative absence of healthy cartilage.

In some patients, however, one or more of the bones of the shoulder are not only arthritic, but have also had previous conditions that have caused bone to wear away. In such cases, there may not be sufficient bone to adequately affix a prosthetic implant to the bone, or the bones may have been worn such that the orientation of a joint replacement cannot not be satisfactorily determined to ensure a positive patient outcome.

Specifically, the glenoid bone is subject to increased wear due to bone arthritic conditions of the joint, and due to alteration of normal soft tissue envelope surrounding the joint. In this case, the orientation of the face of the glenoid portion of the scapula bone may be altered so that the humeral bone is no longer appropriately apposed to the glenoid surface. In the case where the glenoid is severely worn, there are two risks a surgeon must balance in an attempt to improve shoulder function and pain relief.

First, if the optimal orientation of the diseased but treated shoulder is not found and replicated with the prosthesis the patient may experience more operative complications related to subluxation or dislocation of the replaced shoulder joint. This can occur either due to passive inputs to the shoulder (e.g., leaning against it, or lying in bed), or due to active firing of surrounding soft tissue which is not able to be constrained by the replaced joint surfaces.

Additionally, the fixation of the replacement prosthesis to the native patient bone can be problematic. Frequently, in order to counteract the risks associated with joint subluxation and dislocation described above, it is necessary for a surgeon to orient or position the replacement prosthesis or implant in a position better suited to resist imbalanced muscle forces. In such cases, separation forces between the implant and the bone can increase, which in turn can increase the potential for loosening of the joint prosthesis in the bone. Implant loosening can be related to accelerated implant wear, bone erosion, increased tissue inflammation, joint synovitis, and pain.

In patients that have undergone shoulder replacement surgery, range of motion and strength are dependent on shoulder kinematics, which are in turn dependent on a host of factors. Such factors can include for example implant size, implant position, the design of implant shape, the joint line and soft tissue tension. In some cases it can be difficult to predict optimal implant size and position/orientation using currently available guides and implants. Often times a surgeon finds that there are too many variables to manage at one time. Moreover, the size choices of implants can be limited to the lowest number of practically functional groups to reduce economic burden to health care system.

In an attempt to overcome some of the above noted challenges, various implant designs and methodologies have been developed. However, such attempted solutions have been inferior because they are of significant cost, require time to develop, include increased risk of implant failure, and rely on human judgment of potential outcomes pre-operatively.

There are many factors that can affect the optimal positioning of the shoulder implants during replacement surgery. For example, such factors can include the patient size, relative bone wear, soft tissue strength and condition, six degrees-of-freedom positioning of the glenoid and/or the humeral prosthesis, selected implant size, preoperative patient activity and strength levels, post-operative treatment protocols, size and density of patient bone. Additional factors may include patient smoking status, concomitant handicaps or patient problems. It can be quite difficult for a surgeon to understand and balance these factors simultaneously. In addition, only a few of these factors are able to be controlled by the surgeon. Finally, each factor does not necessarily have an equally weighted impact on patient outcome. Nevertheless, it is considered that the implant size, position, orientation and bone preparation of the glenoid and the humerus have a significant impact on the surgical outcomes.

A factor that further complicates, or makes more difficult, the surgeons task of optimally placing a replacement component or implant to counteract these risks is the fact that the condition of the scapula is such that few landmarks exist for the surgeon to comprehend the implant position within the bone. Thus, frequently a surgeon might find that the implant position is not replicated the way it was envisioned during the surgical intervention.

Others have attempted to improve a surgeon's chance of providing successful patient outcomes by providing operative techniques and tools. What is missing, however, is the ability to fully understand and incorporate all necessary factors to optimize the implant selection and placement. Specifically, in some embodiments, the success of the surgery is highly dependent on both the selection of the matching humeral prosthesis, as well as positioning of this prosthesis, as well as the soft tissue status before the surgery. There are no previous attempts at including these factors in surgical planning and implant design.

A challenge commonly faced by surgeons attempting to optimally position the proximal articulating portion of the humeral implant is that the offset between the diaphyseal portion of the bone and the metaphyseal portion of the bone is not well accommodated for in the prosthesis design. Commonly, implants are provided such that for a given size implant, there is a limited offset available based on the diaphysis axis, even though it is widely known that the offset between the diaphysis and metaphysis varies from patient to patient. This causes a problem in that the interaction of the stem in the diaphysis can overcome the positioning of the implant such that the articular portion of the implant is not perfectly positioned. What is needed is a device that can be configured through the following method, which includes analysis of patient anatomy and condition; determination of best size and position of articular surface in the glenoid and the humerus; determination of the best fixation component to position articular surface where needed according to the determined best size and position; assessment of diaphyseal size and position in relationship to the metaphysis; selection of optimal size and position of stem component for optimal fixation, irrespective of articular surface component position; determination of positional relationship between two components; conception of patient specific adapter component that would affix the stem and articular surface components together in their desired positions; and manufacture of patient specific adapter component.

SUMMARY OF THE INVENTION

Aspects of the present invention provide implants and methods for replacing a shoulder joint.

In one aspect, provided herein is a humeral prosthetic implant. The implant includes a proximal cup portion and a distal stem portion, wherein the proximal cup portion is joined to the distal stem portion at at least one of an offset and an angle relative to a longitudinal axis of the distal stem portion.

In one another aspect, provided herein is a humeral prosthetic implant. The implant includes a proximal cup portion and a distal stem portion, wherein the proximal cup portion is joined to the distal stem portion at a desired offset and/or angle configured based on an analysis of the humeral diaphysis and/or metaphysis offset in a patient.

In another aspect, provided herein is a humeral prosthetic implant. The implant includes a proximal cup component with a distal engagement feature and a stem component with a proximal engagement feature. The distal engagement feature of the proximal cup and the proximal engagement feature of the stem are configured to join the stemless cup component to the stem component at a desired offset and/or angle.

In yet another aspect, provided herein is a humeral prosthetic implant. The implant includes a proximal cup component, a stem component, and an adapter configured to join the proximal cup component with the stem component, wherein the adapter is configured to join the stem component to the stemless cup at a desired offset and/or angle.

In a further aspect, provided herein is a pre-operative planning method for designing a humeral prosthetic implant. The method includes analyzing of one or more of humerus stem size, length, head diameter, head height, head offset, rotation (axial), humeral diaphysis and/or metaphysis offset of a patient to be treated.

In another aspect, provided herein is a method of treating a patient. The method includes providing a patient to be treated, completing pre-operative planning for designing a humeral prosthetic implant device, creating a humeral prosthetic implant based upon pre-operative planning, and treating the patient using and/or surgically implanting the humeral prosthetic implant.

In yet another aspect, provided herein is a pre-operative planning and shoulder surgery kit. The kit includes a set of instructions for performing measurements for creating a humeral prosthetic implant device and one or more humeral prosthetic implant devices. The humeral prosthetic implant devices include a proximal cup component, a stem component, and a dual taper adapter configured to join the stemless cup component with the stem component.

These, and other objects, features and advantages of this invention will become apparent from the following detailed description of the various aspects of the invention taken in conjunction with the accompanying drawings.

BRIEF DESCRIPTION OF THE DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which.

DETAILED DESCRIPTION FOR CARRYING OUT THE INVENTION

Figure 1:
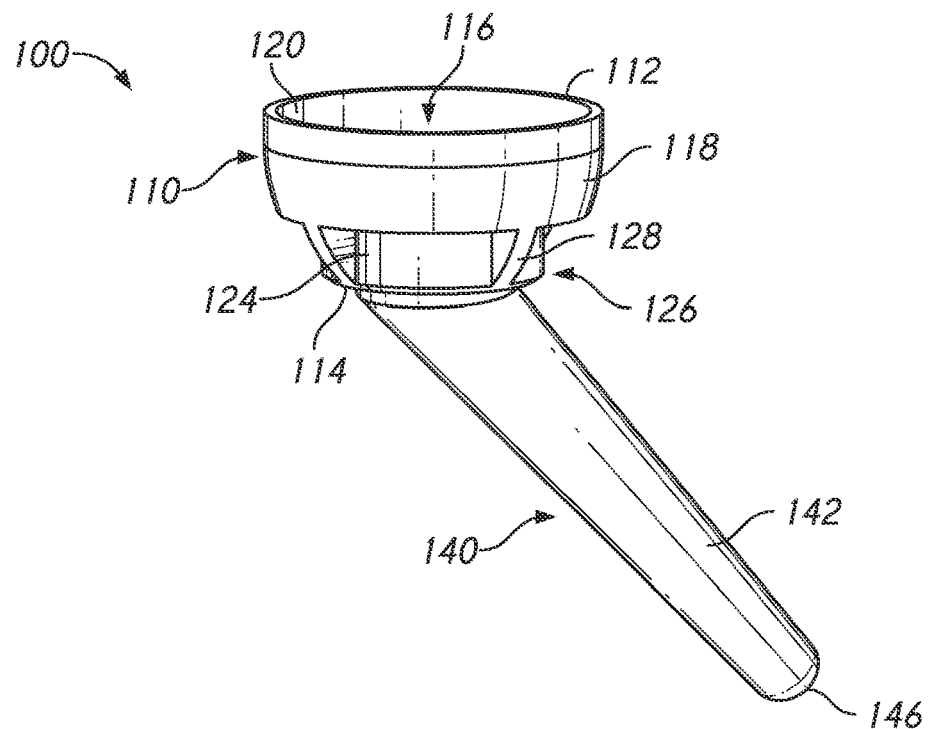
FIG. 1 is a top perspective view of an embodiment of a reverse humeral prosthesis or implant, in accordance with an aspect of the present invention.
Figure 2:
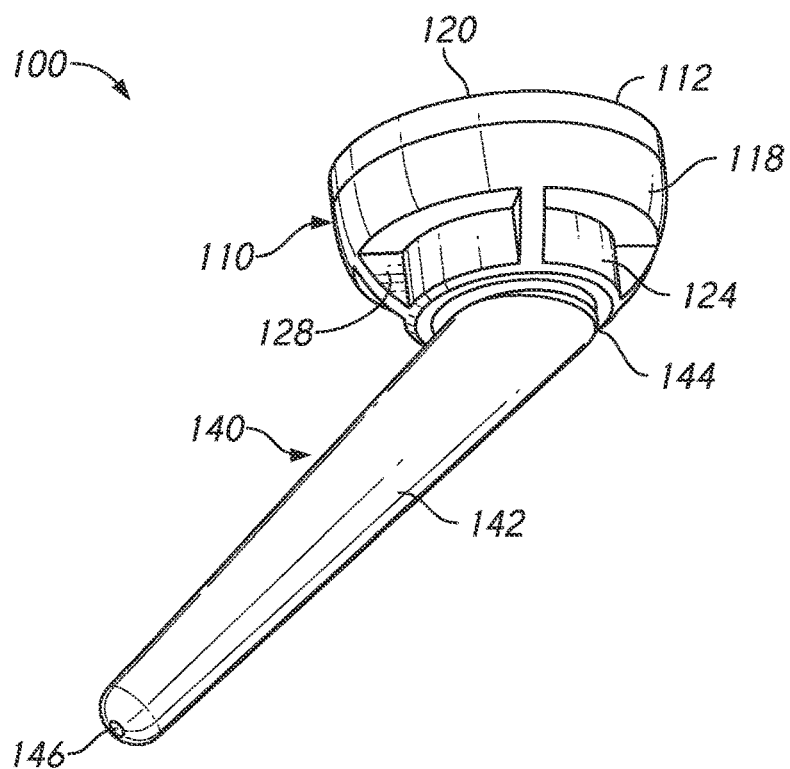
FIG. 2 is a bottom perspective view of the implant of FIG. 1, in accordance with an aspect of the present invention.
Figure 3:
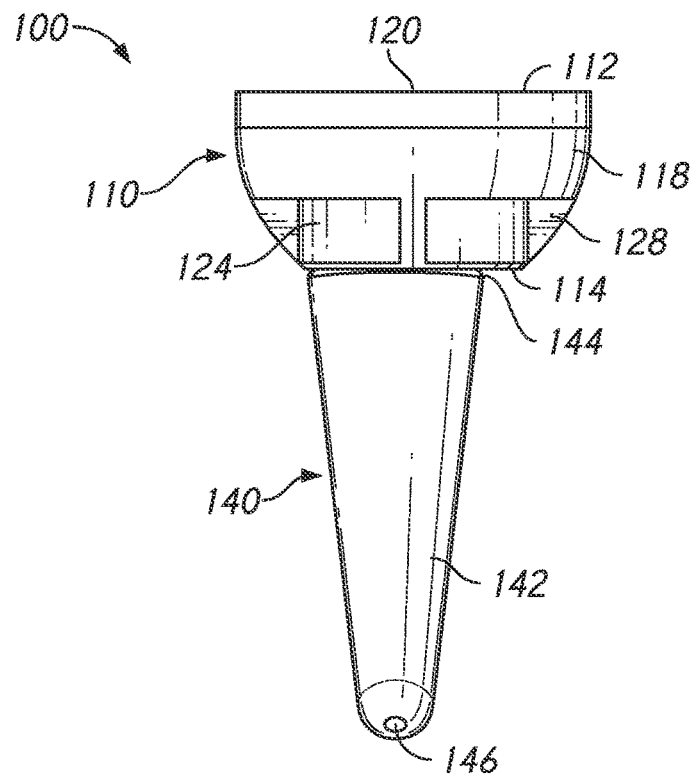
FIG. 3 is a front view of the implant of FIG. 1, in accordance with an aspect of the present invention.
Figure 4:
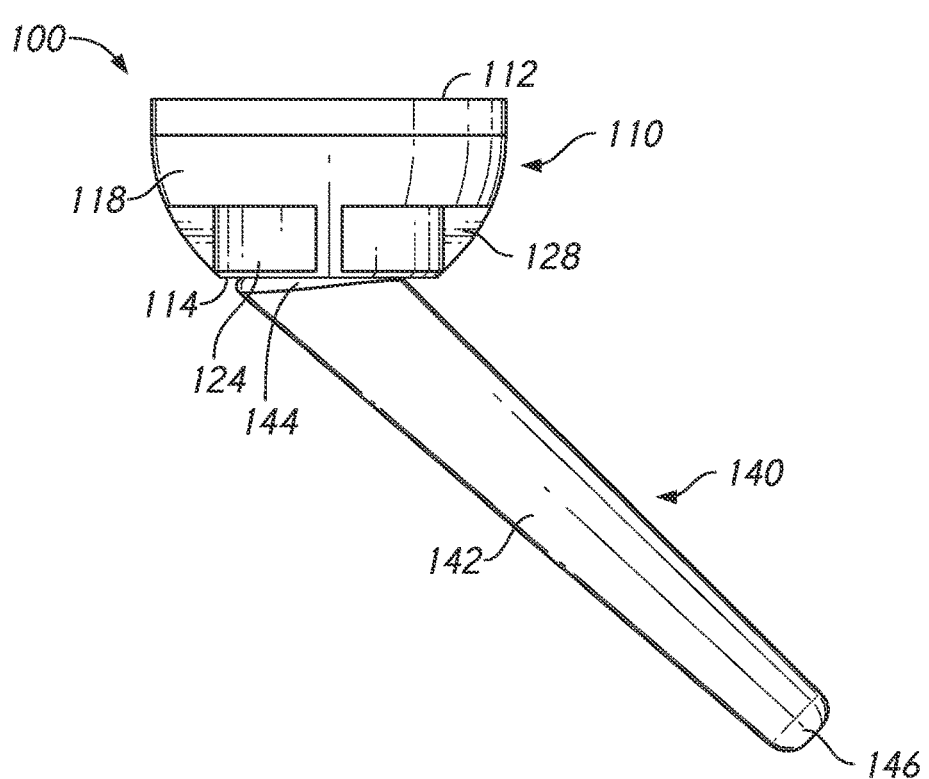
FIG. 4 is a side view of the implant of FIG. 1, in accordance with an aspect of the present invention.

Disclosed herein are methods, systems and devices for pre-operatively planned shoulder surgery guides and implants. Methods, systems and devices are provided for the replacement of the shoulder joint wherein the conditions of the humeral and soft tissue envelop is taken into consideration. More specifically, what is considered is that the shape and position of the glenoid and/or humeral implants is not based solely on what can be seen and measured on the scapula, but can be chosen, designed, planned and placed with incorporation of the same information related to the humerus. After all, the shoulder is a two part joint, wherein both parts work in conjunction with one another, and the factors that affect performance of the device include factors from both sides of the joint.

In this detailed description and the following claims, the words proximal, distal, anterior, posterior, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

Similarly, positions or directions may be used herein with reference to anatomical structures or surfaces. For example, as the current implants, devices, instrumentation and methods are described herein with reference to use with the bones of the shoulder, the bones of the shoulder and upper arm may be used to describe the surfaces, positions, directions or orientations of the implants and methods. Further, the implants and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the implants and methods, and the aspects, components, features and the like thereof, described herein with respect to the right shoulder may be mirrored so that they likewise function with the left shoulder and vice versa. Further, the implants and methods, and the aspects, components, features and the like thereof, disclosed herein are described with respect to the shoulder for brevity purposes, but it should be understood that the implants and methods may be used with other bones of the body having similar structures.

Referring to the drawings, wherein like reference numerals are used to indicate like or analogous components throughout the several views, and with particular reference to FIGS. 1-30, there are illustrated exemplary embodiments of reverse humeral prostheses or implants 100, 200, 300, 400. Insertion of the implant 100, 200, 300, 400 may be optimized using a preoperative plan. The preoperative plan may provide the ability to design and surgically implant a reverse humeral prosthesis 100, 200, 300, 400 that is configured or sized and shaped to have a predetermined, neck angle and/or offset. In order to achieve optimal articular positioning, there must be recognition of and accommodation for the humeral diaphysis and metaphysis offset. Appropriate sizing, placement and orientation of the prosthesis 100, 200, 300, 400 is crucial to successful outcomes, because misaligned, oversized or "overstuffed" replacement shoulders are more likely to dislocate, loosen, be painful, and/or have decreased range of motion. In addition, replaced joints where the orientation of the prostheses 100, 200, 300, 400 is improper increases the likelihood of implant dislocation and loosening.

The reverse humeral implants 100, 200, 300, 400 may also be designed and manufactured to specifically match a patient's anatomy, including humeral and/or glenoid implant size and shape customized to the given patient. The customized implants 100, 200, 300, 400 may be designed and manufactured taking into account one or more of the following factors: (1) assessment of the reverse humeral implant fit to the humeral bone; (2) relative hardness of the patient bone preoperatively; (3) height and diameter of the reverse humeral cup; (4) orientation, or "offset" of the reverse humeral cup; and (5) optimal bone removal for preservation of soft tissue insertion and attachment. The implants 100, 200, 300, 400 may be, for example, adaptable reverse humeral implant systems or kits, which may include a stemless reverse cup 110, 210, 310, 410, a stem 140, 230, 330, 440, and an intermediate adapter 160, 250, 350, 460 configured or sized and shaped to join or align the stemless reverse cup 110, 210, 310, 410 with the stem 140, 230, 330, 440. The stem 140, 230, 330, 440 may be, for example, a relatively short stem as described in greater detail below. The adapter 160, 250, 350, 460 may be, for example, configured or sized and shaped to achieve a desired offset or angle between the cup 110, 210, 310, 410 and stem 140, 230, 330, 440. The adapter 160, 250, 350, 460 may also, for example, be a dual taper adapter that is configured or sized and shaped to provide for angle customization and/or offset customization. The angle and/or offset customization may take into account, for example, patient anatomy, humeral size, humeral diaphysis, and metaphysis offset. For example, the adapter 160, 250, 350, 460 may be configured or sized and shaped based on the following: (1) position the metaphysis; (2) assess the diaphysis; (3) determine the optimal humeral implant; (4) conceive the adapter based on these assessments; and (5) confirm constraints are met. The adapter 160, 250, 350, 460 may also be configured or sized and shaped based on the measurements for improved fixation strength and/or overall construct range of motion.

Referring now to FIGS. 1-10, the reverse humeral prosthesis or implant 100 is shown. The implant 100 includes a stemless reverse cup 110 for implantation in the proximal part of a humerus 190, a stem 140, and an adapter 160 to couple the cup 110 and the stem 140. Unlike an anatomic orientation of a humerus where the head on the humerus includes a convex surface that articulates against a concave surface of a glenoid, a reverse humeral implant provides a concave surface on the humeral head configured or sized and shaped to articulate with a convex head attached to the glenoid region of the scapula.

Figure 5:
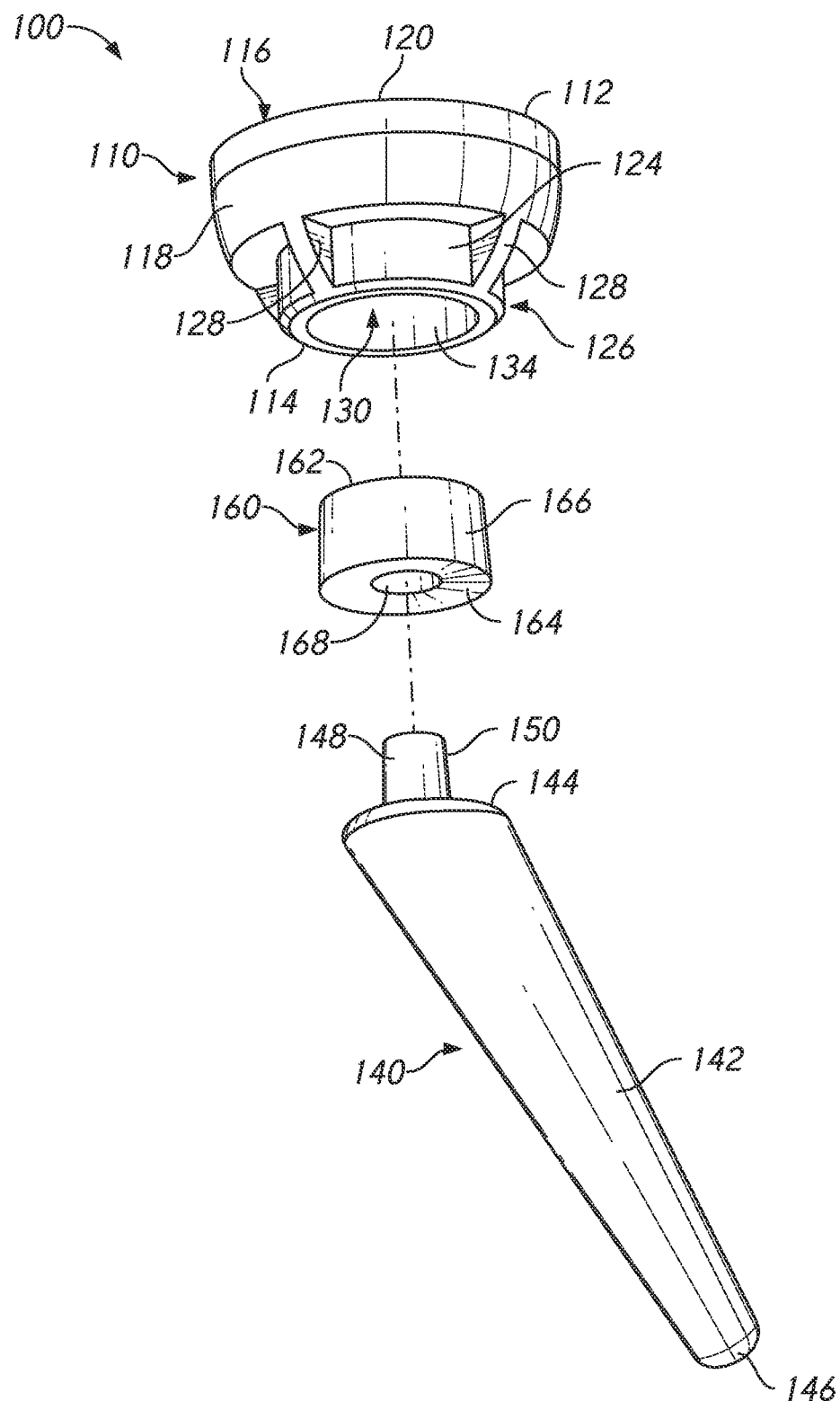
FIG. 5 is an exploded bottom perspective view of the implant of FIG. 1, in accordance with an aspect of the present invention.
Figure 6:
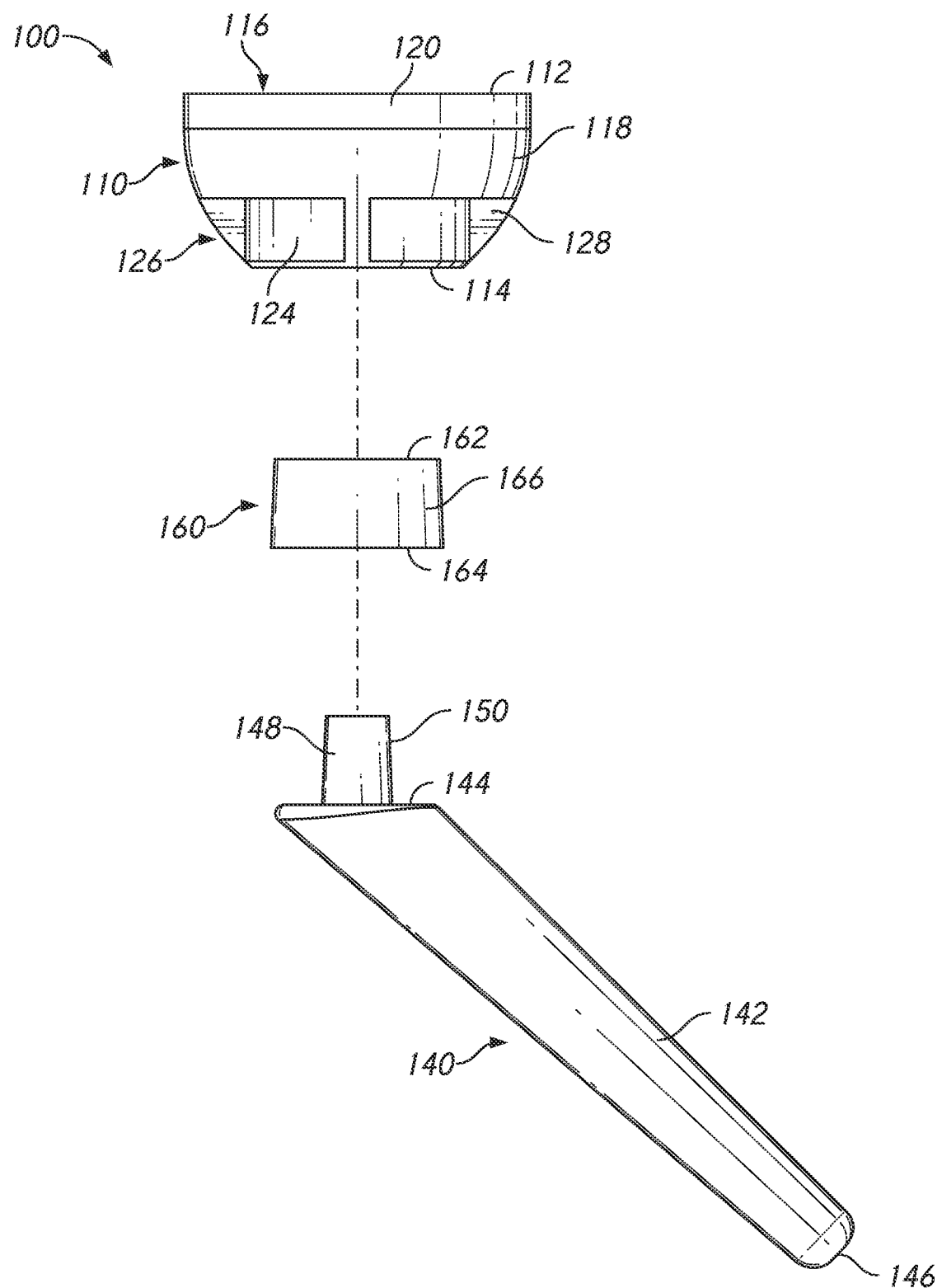
FIG. 6 is an exploded side view of the implant of FIG. 1, in accordance with an aspect of the present invention.
Figure 7:
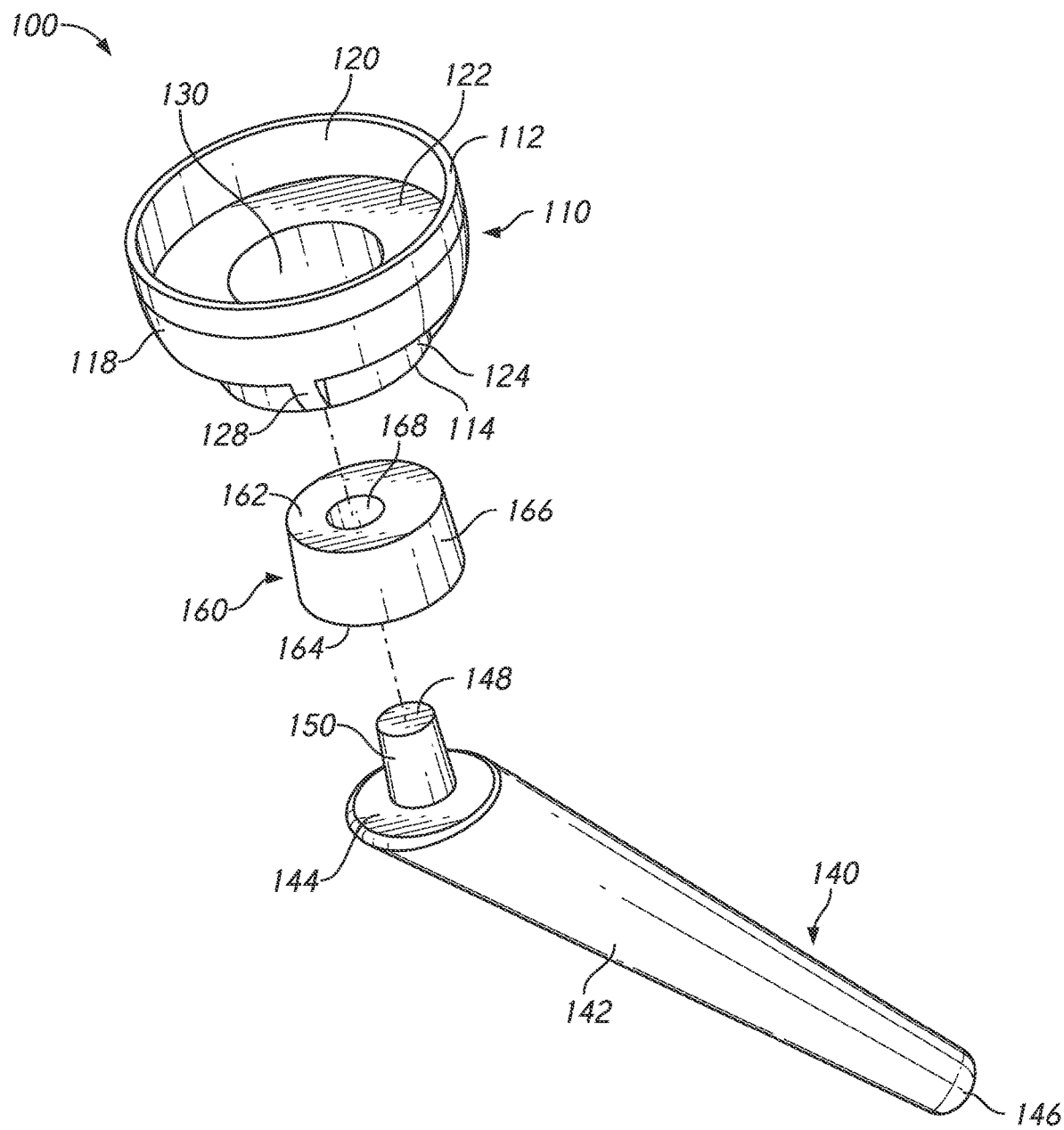
FIG. 7 is an exploded top perspective view of the implant of FIG. 1, in accordance with an aspect of the present invention.

As shown in FIGS. 1-7, the stemless reverse cup 110 may have a first end 112 and a second end 114. The terms "stemless reverse cup," "proximal reverse cup," "proximal cup," "proximal cup portion," "proximal cup component" and "cup" may be used interchangeably herein as they each refer to the portion of a shoulder implant that engages the glenoid or glenoid replacement. The cup 110 may include a generally cup-shaped housing 116 with an outer cylindrical wall 118 defining a recess 122 on an upper surface 120 and a base portion 126 extending away from a bottom surface, lower surface or backside 124 of the cup-shaped housing 116, as shown in FIG. 7. The recess 122 may extend into the housing 116 from the first end 112 toward the second end 114 of the cup 110. The base portion 126 may extend out from the second end 114 of the cup 110. The recess 122 may be configured or sized and shaped to receive and securely hold, for example, a cup liner (not shown) made of polyethylene or another material as known by one of skill in the art. The cup liner (not shown) may be configured or sized and shaped to snap fit into the recess 122. The cup liner (not shown) may also have a concave articular surface to allow for the cup liner (not shown) to articulate with a convex head attached to, for example, the glenoid part of the scapula. The stemless reverse cup 110 may also include, for example, ribs, fins, or projections 128 extending away from the bottom surface 124. The ribs 128 may include a surface or rib-like structure projecting from the outer cylindrical wall 118 of the reverse cup 110. The ribs 128 may project from the surface of the outer cylindrical wall 118 in, for example, a generally perpendicular orientation. The ribs 128 may also be configured or sized and shaped to provide rotational control under a torsional load, i.e., resist or prevent twisting or turning of the reverse cup 110 within the implant site after implantation. The stemless reverse cup 110 may optionally be made of a metallic material, such as for example, stainless steel, cobalt-chromium, titanium alloy, or any other like material as known by one of ordinary skill in the art. It is also contemplated that the stemless reverse cup 110 may include a metallic and/or biological porous coating to enhance bony integration. The biological porous coating may be, for example, pure HA, pure TCP, or a mix of HA/TCP.

The stemless reverse cup 110 may be formed through additive manufacturing of a monolithic component. The monolithic component may include an internal plain wall partially covered on the external surfaces with a porous metallic structure. Each of the porous structure sections may include an annular plain surface distally helping the surgeon to drive the implant 100 into the bone. The stemless reverse cup 110 may also be a monolithic component with a concave, spherical articular surface on an upper surface 120 of the reverse cup 110. The concave, spherical articular surface may articulate with a convex spherical head attached to the glenoid part of the scapula and on a base portion a surface enhanced for bony integration. The monolithic cup 110 may be made of, for example, a polymer, such as, PEEK, polyethylene, polyurethane, and the like as known by one of skill in the art. The monolithic cup 110 may also include, for example, a metallic coating on the bony facing surface.

With continued reference to FIG. 7, the recess 122 may also be configured or sized and shaped to receive and securely hold a universal adapter (not shown) which may be configured or sized and shaped to snap fit into the recess 122. The universal adapter (not shown) may have a convex surface which articulates against a concave surface of a glenoid or which articulates with a concave surface attached to the glenoid part of the scapula. The universal adapter (not shown) may also include a means for engaging another component that has a convex surface.

Referring now to FIG. 5, the lower portion or backside 124 of the stemless reverse cup 110 may also include an opening 130. The opening 130 may be configured to or sized and shaped to receive an adapter 160. The opening 130 may include, for example, a receiving portion 132 built into the lower portion of the cup 110, as shown in FIG. 7. The receiving portion 132 may be, for example, substantially cylindrical. The opening 130 may have an inner wall with, for example, a tapered diameter (not shown) and may be configured to receive a similarly tapered adapter 160, as shown in FIG. 6. The tapered configuration enables the adapter 160 to be press fit or otherwise forced into the opening 130 of the reverse cup 110 to securely engage the adapter 160 with the cup 110 during implantation of the prosthetic device 100. Alternatively, or in addition, the implant 100 may include a connection means (not shown) between the adapter 160 and the cup 110. The connection means (not shown) may include, for example, a screw, a press fit configuration without a taper, a press fit configuration with a taper, and/or a snap ring.

Figure 8:
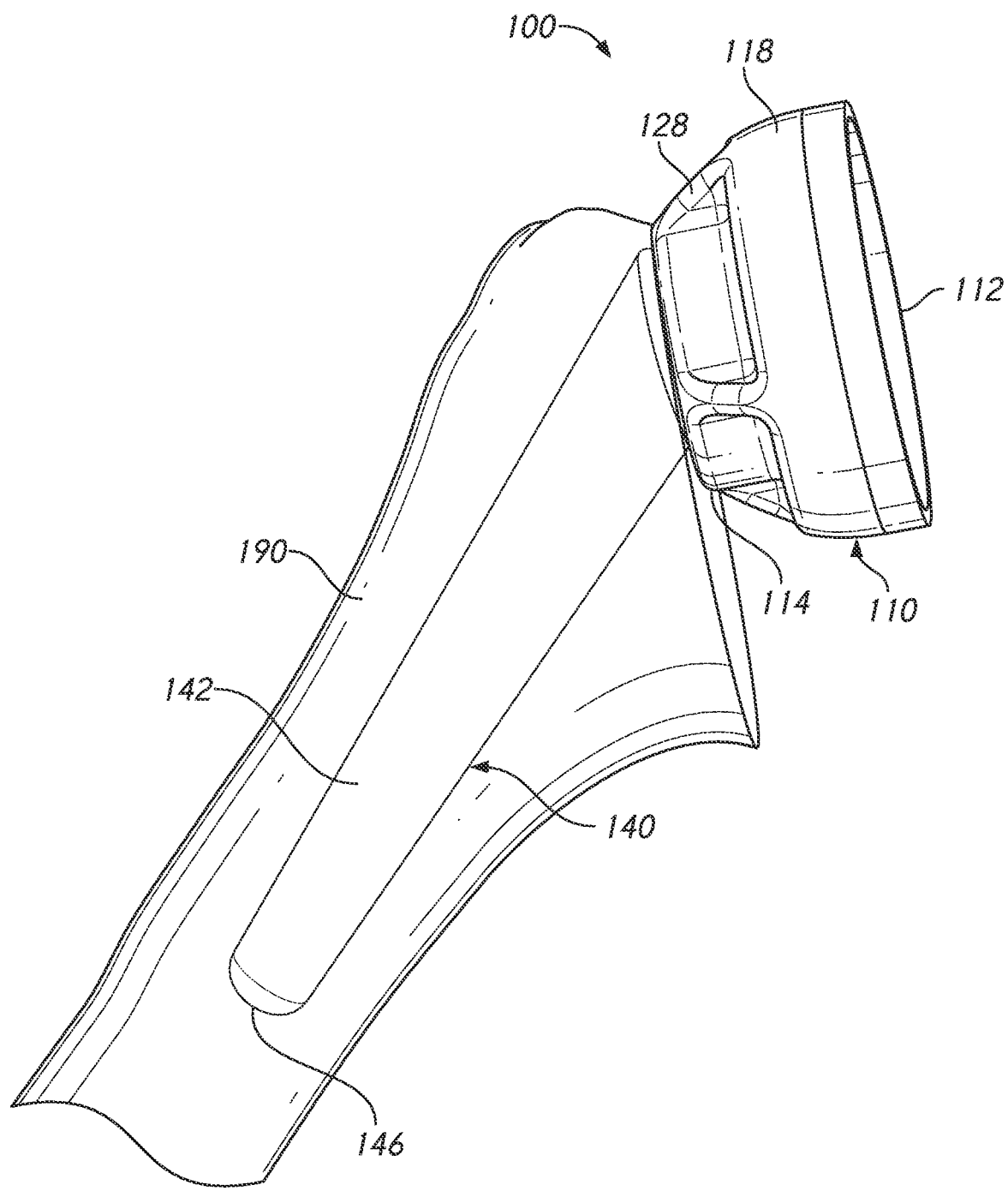
FIG. 8 is a side view of the implant of FIG. 1 inserted into a portion of a humerus in a first position, in accordance with an aspect of the present invention.
Figure 9:
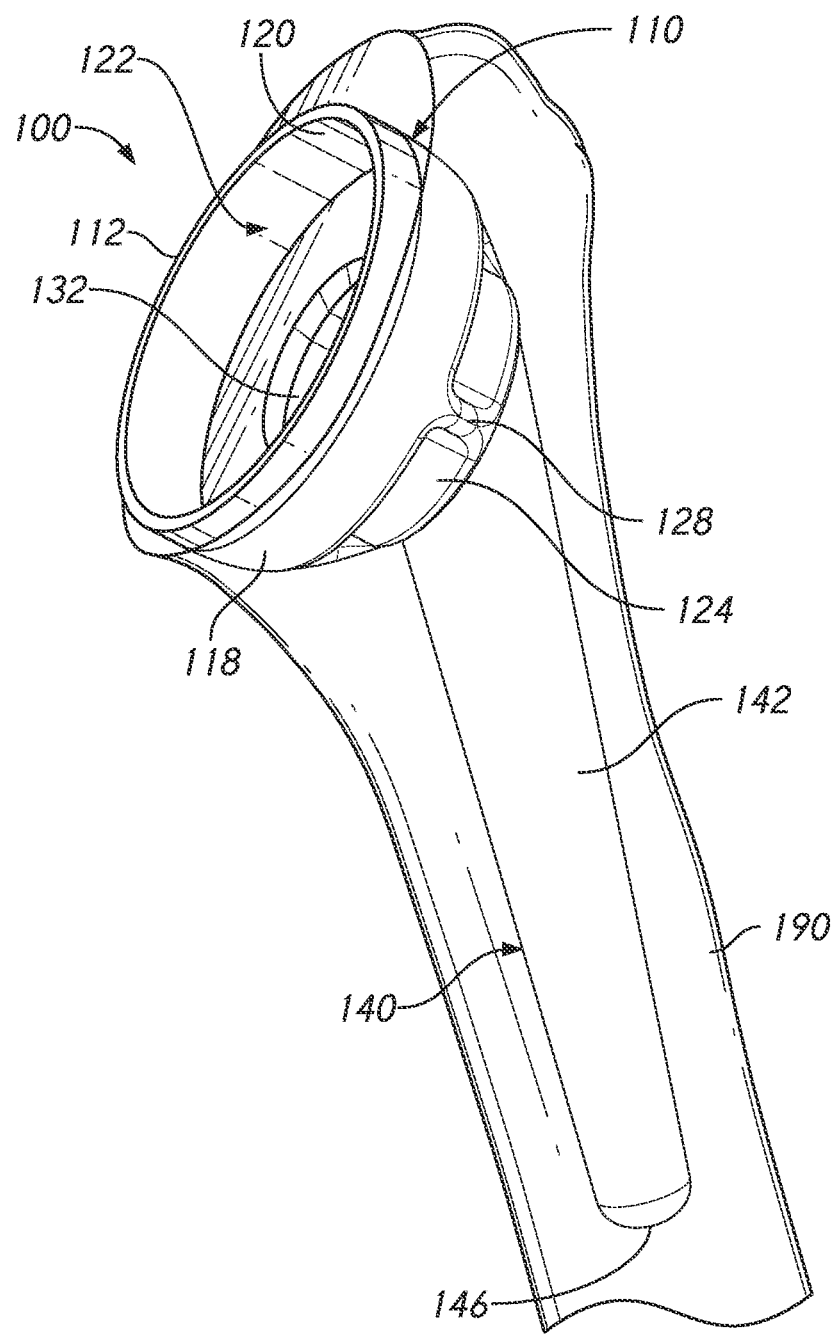
FIG. 9 is a side perspective view of the implant of FIG. 1 inserted into a portion of a humerus in a second position, in accordance with an aspect of the present invention.
Figure 10:
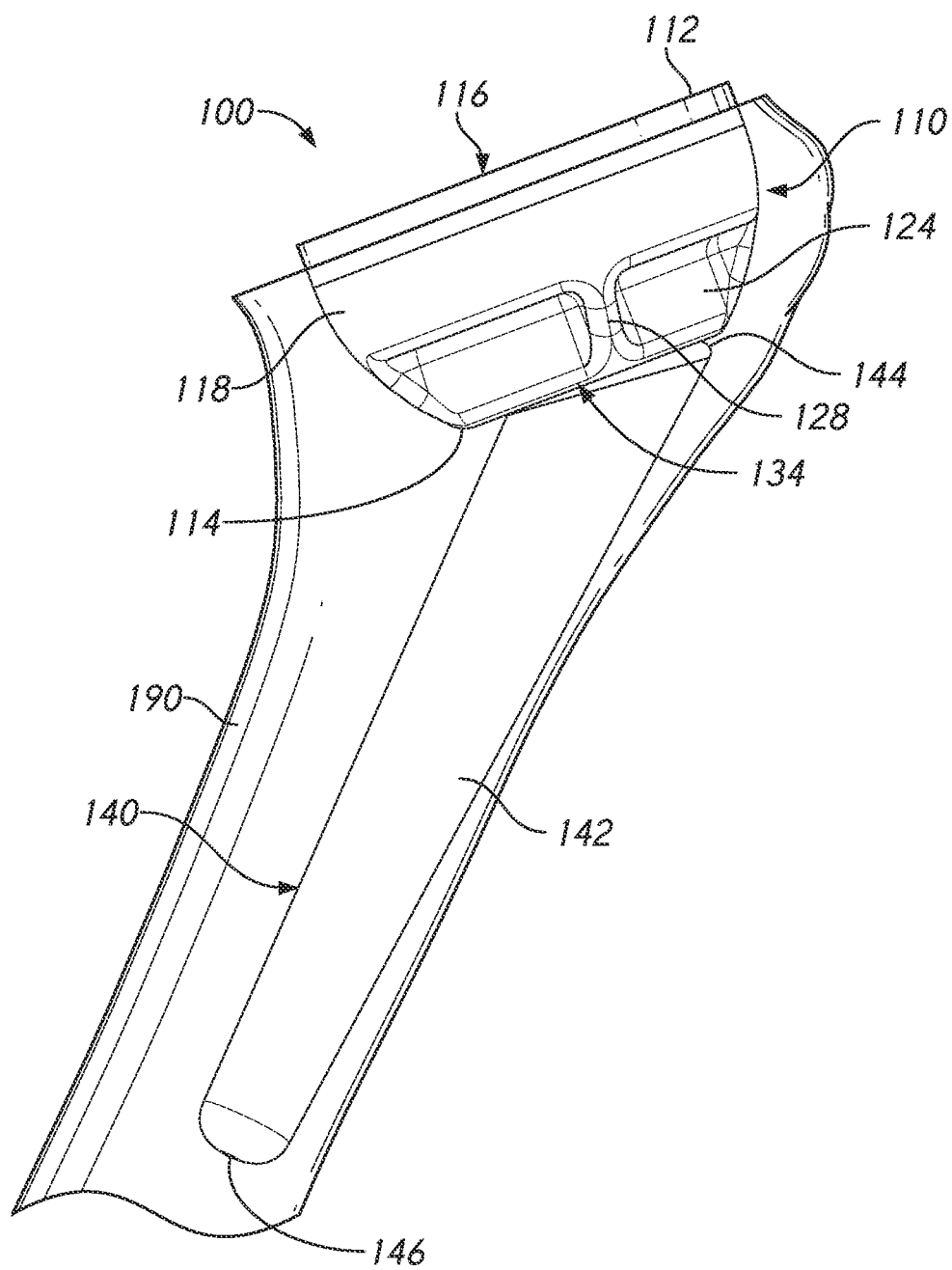
FIG. 10 is a side view of the implant of FIG. 1 inserted into a portion of a humerus in the second position, in accordance with an aspect of the present invention.
Figure 12:
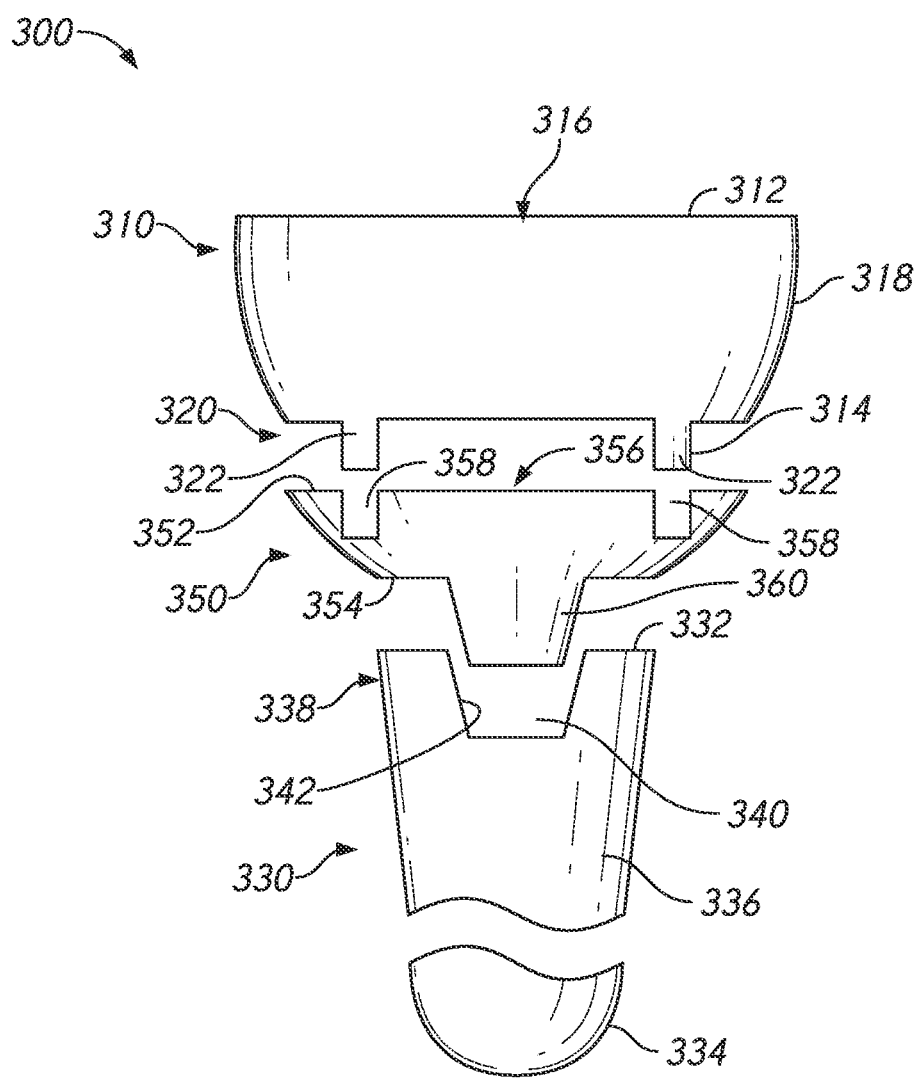
FIG. 12 is a cross-sectional side view of yet another embodiment of a reverse humeral prosthesis or implant, in accordance with an aspect of the present invention.
Figure 13:
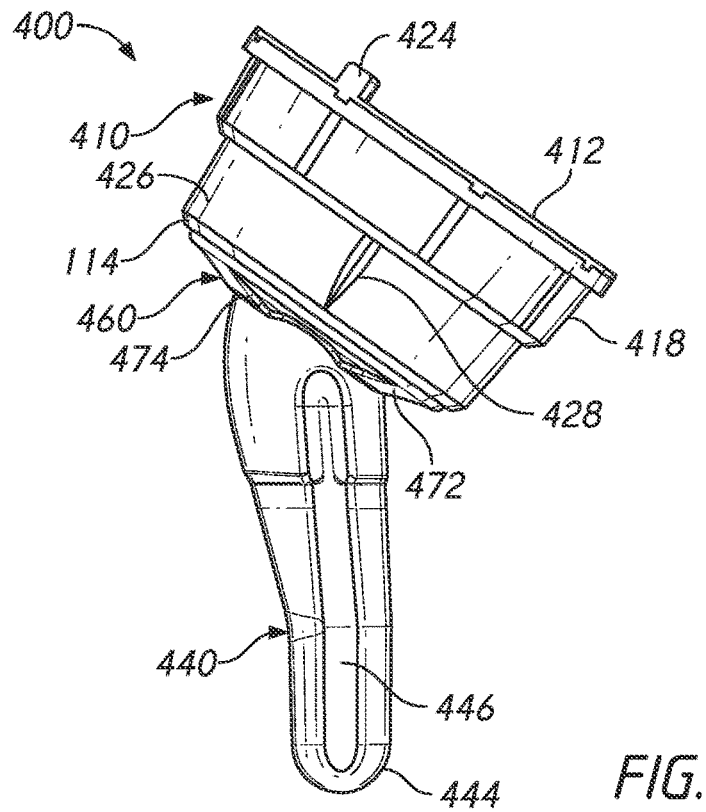
FIG. 13 is a side view of another embodiment of a reverse humeral prosthesis or implant, in accordance with an aspect of the present invention.
Figure 14:
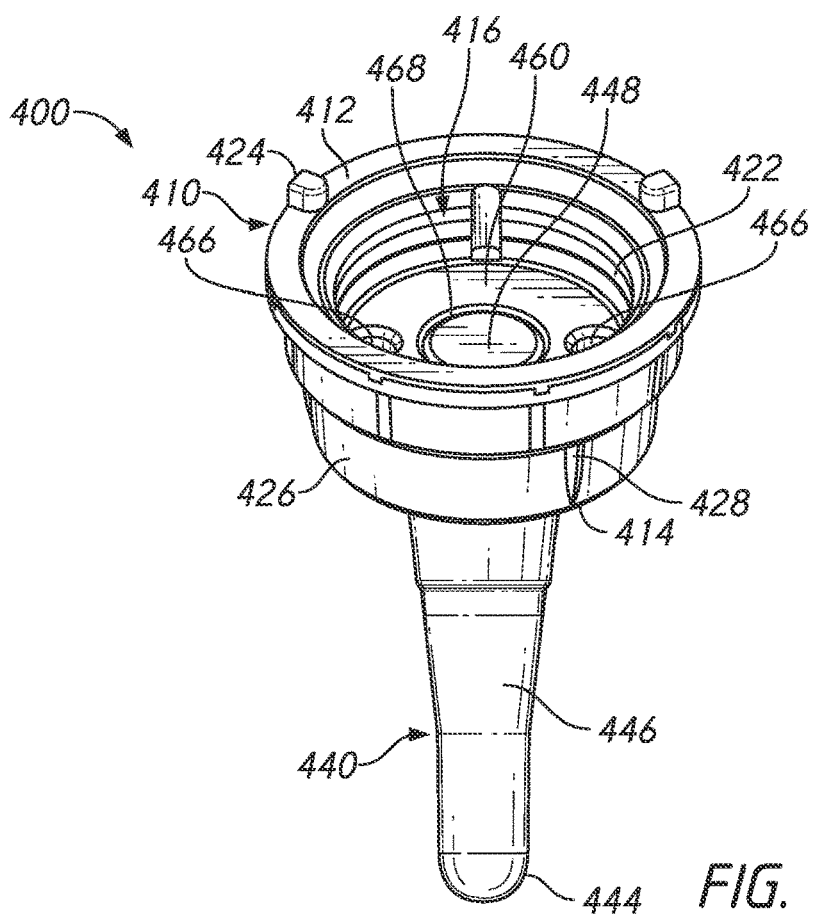
FIG. 14 is a front view of the implant of FIG. 13, in accordance with an aspect of the present invention.
Figure 15:
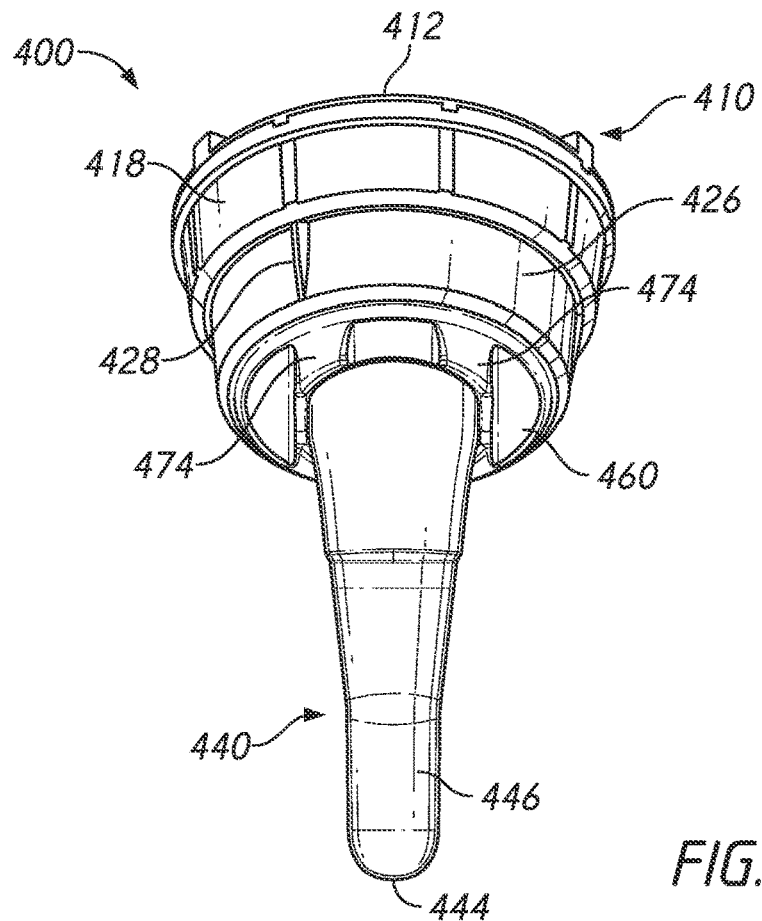
FIG. 15 is a back view of the implant of FIG. 13, in accordance with an aspect of the present invention.
Figure 16:
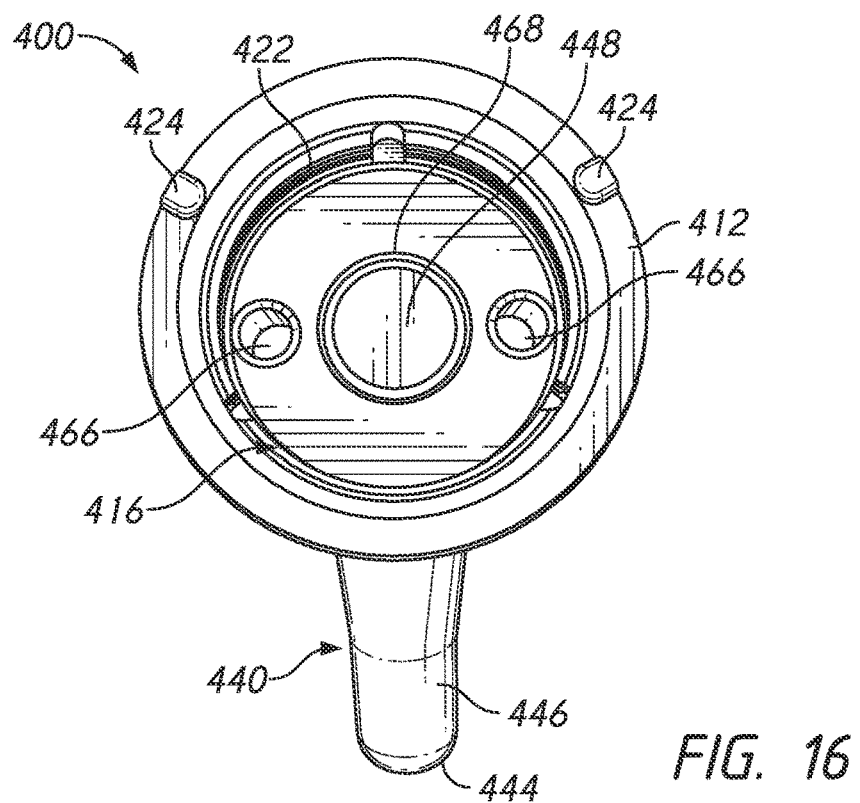
FIG. 16 is a top view of the implant of FIG. 13, in accordance with an aspect of the present invention.

As shown in FIGS. 5 and 7, the reverse humeral implant 100 may also include the stem 140. The terms "stem," "distal stem," "distal stem portion," "stem portion," "distal stem component," "stem component" may be used interchangeably herein as they each refer to the portion of the shoulder implant that is inserted into at least a portion of the humeral canal. The stem 140 may be configured to be implanted within the humerus 190, for example, extending into the epiphysis and diaphysis of the humerus 190, as shown in FIGS. 8-10. The stem 140 may be, for example, a relatively short stem compared to the stems used in existing traditional prosthetic devices. The short stem 140 may be, for example, less than about 80 mm, whereas a typical stem is about 80 mm to about 120 mm, and a long stem is about 120 mm or more. The stem 140 of the reverse humeral implant 100 may include a shaft portion 142 with a first end 144 configured or sized and shaped to adjoin the adapter 160 and a second terminal end 146. The first end 144 may include, for example, a joining member 148 configured or sized and shaped to press fit or otherwise adjoin with the adapter 160. The joining member 148 may include a substantially cylindrical structure 150 projecting from the first end 144 of the stem 140. The cylindrical structure 150 of the joining member 148 may have, for example, a tapered outer diameter and be configured or sized and shaped to engage a similarly cylindrical and tapered opening 168 in the adapter 160. As shown in FIGS. 1-10, the joining member 148 may also project from the first end 144 of the stem 140 at a desired angle to orient the stem 140 in a desired position with respect to the adapter 160 and the cup 110. It is also contemplated that the joining member 148 may be, for example, a female joining member configured or sized and shaped to engage a similarly male structure projecting from the distal end of the adapter, such as shown in FIG. 12 and described in greater detail below.

In one embodiment, the adapter 160 of the reverse humeral implant 100 may include an intermediate dual taper. The intermediate dual tapered adapter 160 may be configured or sized and shaped to join or align the stemless reverse cup 110 with the stem 140. For example, the outer diameter of the cylindrical member 166 of the adapter 160 may be tapered. Correspondingly, the lower portion or backside 124 of the stemless reverse cup 110 may include an opening 130 configured or sized and shaped to receive the first end 162 of the adapter 160. The opening 130 may include an inner wall 134 with, for example, a tapered diameter that has a taper similar to the taper of the outer diameter of the cylindrical member 166. The tapered outer diameter of the adapter 160 and the tapered inner diameter of the backside 124 of the cup 110 allow for the adapter 160 to be press fitted or otherwise forced into the opening 130 of the reverse cup 110 to securely engage the adapter 160 with the cup 110 during implantation of the prosthetic device 100.

The adapter 160 may also include a substantially cylindrical member 166 with an opening 168 at one end of the cylinder 166. The opening 168 may, for example, extend into only a portion of the adapter 160 or, alternatively, the opening 168 may extend through the entire length of the cylinder 166. As shown in FIG. 5, the opening 168 may be configured or sized and shaped to receive a joining member 148, for example, a male joining member, of the stem 140. The opening 168 of the adapter 160 may include a cylindrical opening with a diameter that is tapered. The tapered opening 168 may be configured or sized and shaped to receive a similarly tapered joining member 148 of the stem 140. The tapered inner diameter of the adapter 160 may be, for example, press fit with the tapered joining member 148 of the stem 140. The tapered outer diameter and tapered inner diameter of the adapter 160 may be referred to as a dual-tapered design. Each taper of the dual-tapered design may be, for example, infinitely dialable or adjustable. Alternatively, engagement of at least one of the tapers of the dual-tapered design may be restricted to a discrete number of angular positions.

With continued reference to FIGS. 1-10, the adapter 160 may be configured to achieve a desired offset or angle between the cup 110 and stem 140. For example, the dual taper adapter 160 may be configured or sized and shaped to provide angle customization and/or offset customization. The angle customization and/or offset customization may take into account one or more of, for example, the patient anatomy, humeral size, humeral diaphysis, and metaphysis offset. The adapter 160 may also be, for example, configured to achieve a desired offset or angle between the cup 110 and stem 140. For example, the opening 168 may be positioned offset from a center point or central axis of the adapter 160. Further, the exterior size and shape of the adapter may provide the angulation of the cup 110 with respect to the stem 140. For example, the cup 110 may be offset or angled with respect to a central axis of the joining member 148 of the stem 140. Alternatively or in addition to the exterior size and shape of the adapter 160 providing the angulation of the implant 100, the opening 168 may be positioned at an angle to the central axis of the adapter 160.

Figure 11:
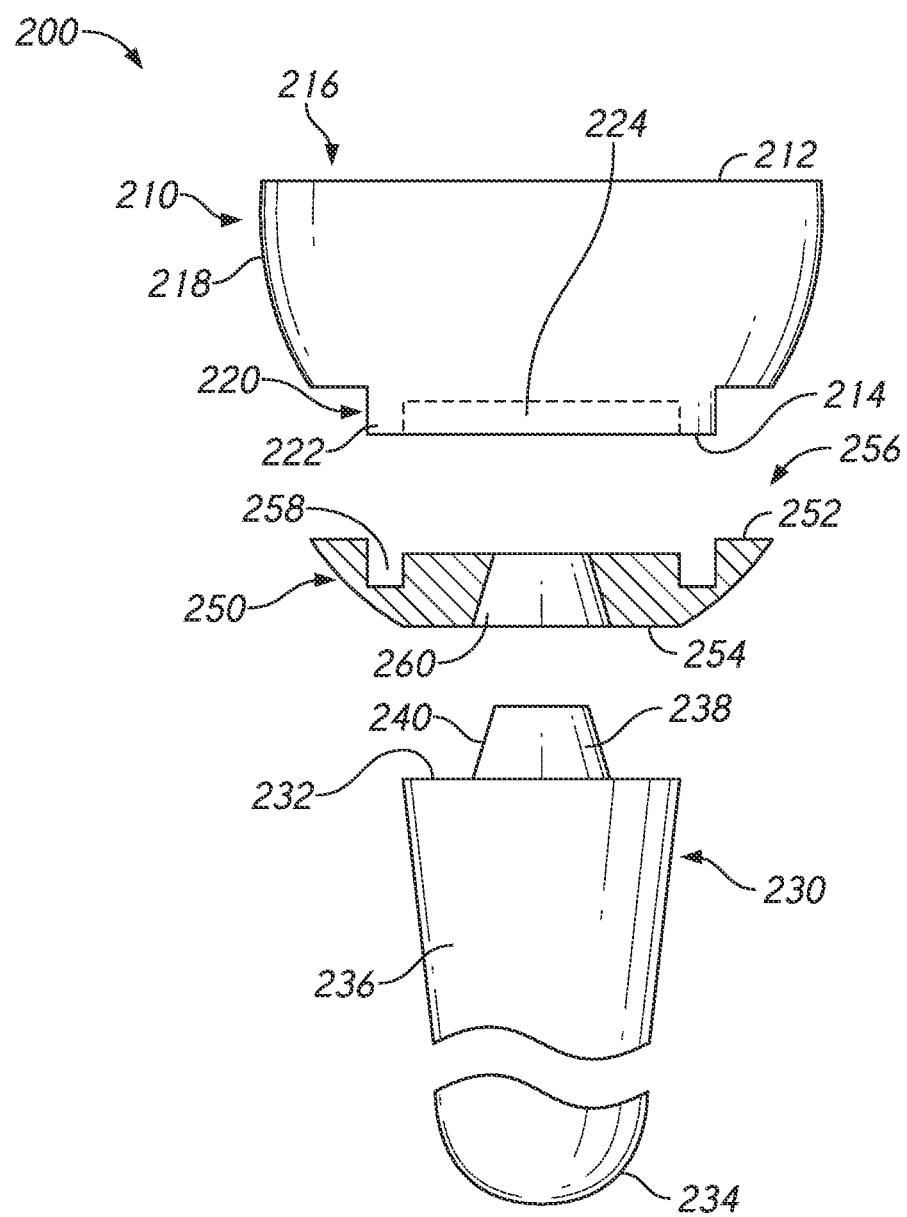
FIG. 11 is a cross-sectional side view of another embodiment of a reverse humeral prosthesis or implant, in accordance with an aspect of the present invention.

Referring now to FIG. 11, an alternative reverse humeral implant 200 is shown. The reverse humeral implant 200 may include a stemless reverse cup 210, a stem 230, and an adapter 250 for coupling the cup 210 and the stem 230. The terms "stemless reverse cup," "proximal reverse cup," "proximal cup," "proximal cup portion," "proximal cup component" and "cup" may be used interchangeably herein as they each refer to the portion of a shoulder implant that engages the glenoid or glenoid replacement. The terms "stem," "distal stem," "distal stem portion," "stem portion," "distal stem component," "stem component" may be used interchangeably herein as they each refer to the portion of the shoulder implant that is inserted into at least a portion of the humeral canal. The cup 210 may include a first end 212 and a second end 214. The cup 210 may also include a recess or interior surface 216 and a backside, exterior surface or outer surface 218. The interior surface 216 may be positioned at and extend into the first end 212 of the cup 210. The interior surface 216 may be a concave surface on the humeral head configured or sized and shaped to receive and articulate with a convex head attached to the glenoid region of the scapula. The backside 218 may extend from the first end 212 to the second end 214 on the exterior of the cup 210 and may be configured or sized and shaped to be received within the head of a humerus. The cup 210 may also include a base portion 220 at the second end 214 of the cup 210. The base portion 220 may extend away from the backside 218 of the cup 210. The base portion 220 may include a flange 222 and a recess or opening 224 extending into the cup 210 inside of the flange portion 222. The flange 222 may be, for example, a circumferential flange extending around at least a portion of the backside 218 of the cup 210.

The stem 230 may have a first end 232 and a second end 234. The stem 230 may include a base portion 236 extending from the second end 234 toward the first end 232 and a joining member 238 at the first end 232. The joining member 238 may be, for example, a male joining member 238 as shown in FIG. 11. The joining member 238 may include an outer diameter 240, for example, smaller than the outer diameter of the base portion 236. The outer diameter 240 of the joining member 238 may, for example, taper as it extends away from the base portion 236.

The adapter 250 may have a first end 252 and a second end 254, as shown in FIG. 11. The first end 252 may be configured or sized and shaped to couple to the cup 210 and the second end 254 may be configured or sized and shaped to couple to the stem 230. The adapter 250 may include a receiving portion 256 with a groove 258 inset into the first end 252 of the adapter 250. The groove 258 may be, for example, a circumferential groove inset into a portion of the adapter 250. The groove 258 may be, for example, designed or sized and shaped to mate with the flange 222 of the cup 210. The adapter 250 may also include an opening 260 extending into at least a portion of the adapter from the second end 254. As shown in FIG. 11, the opening 260 may pass through the entire length of the adapter. The opening 260 may be configured or sized and shaped to receive the joining member 238 of the stem 230. The opening 260 may be, for example, a cylindrical opening with a diameter that is tapered. The tapered opening 260 may be, for example, configured or sized and shaped to receive a similarly tapered joining member 238 of the stem 230 by press fitting the adapter 250 and stem 230 together.

The adapter 250 may also be, for example, configured to achieve a desired offset or angle between the cup 210 and the stem 230. For example, the opening 260 may be positioned offset from a center point or central axis of the adapter 250. Further, the exterior size and shape of the adapter 250 may provide the angulation of the cup 210 with respect to the stem 230. Alternatively or in addition to the exterior size and shape of the adapter providing the angulation of the implant 200, the opening 260 may be positioned at an angle to the central axis of the adapter 250. It is also contemplated that the adapter may be configured for angle customization and/or offset customization based on, for example, patient anatomy, humeral size, humeral diaphysis, and metaphysis offset. The adapter 250 may offset or angle the cup 210 relative to the longitudinal axis of the joining member 238 of the stem 230.

Another alternative reverse humeral implant 300 is shown in FIG. 12. The implant 300 may include a stemless reverse cup 310, a stem 330, and an adapter 350. The terms "stemless reverse cup," "proximal reverse cup," "proximal cup," "proximal cup portion," "proximal cup component" and "cup" may be used interchangeably herein as they each refer to the portion of a shoulder implant that engages the glenoid or glenoid replacement. The terms "stem," "distal stem," "distal stem portion," "stem portion," "distal stem component," "stem component" may be used interchangeably herein as they each refer to the portion of the shoulder implant that is inserted into at least a portion of the humeral canal. The cup 310 may include a first end 312 and a second end 314. The cup 310 may also include a recess or interior surface 316 and a backside, exterior surface or outer surface 318. The interior surface 316 may be positioned at and extend into the first end 312 of the cup 310. The interior surface 316 may be a concave surface on the humeral head configured or sized and shaped to receive and articulate with a convex head attached to the glenoid region of the scapula. The backside 318 may extend from the first end 312 to the second end 314 on the exterior of the cup 310 and may be configured or sized and shaped to be received within the head of a humerus. The cup 310 may also include a base portion 320 at the second end 314 of the cup 310. The base portion 320 may extend away from the backside 318 of the cup 310. The base portion 320 may include at least one tongue, projection, or flange 322 and a recess or opening 324 positioned between the at least one projection 322. The at least one projection 322 may be, for example, a circumferential flange extending around at least a portion of the backside 318 of the cup 310.

The stem 330 may have a first end 332 and a second end 334. The stem 330 may include a base portion 336 extending from the second end 334 toward the first end 332 and a joining member 338 at the first end 332. The joining member 338 may be, for example, a female joining member 338 forming an opening 340, as shown in FIG. 12, for receiving a portion of the adapter 350. The opening 340 may include an interior or inner surface 342 with a diameter, for example, smaller than the outer diameter of the base portion 336. The walls of the interior surface 342 of the opening 340 may, for example, taper as they extend into the base portion 336.

The adapter 350 may have a first end 352 and a second end 354, as shown in FIG. 12. The first end 352 may be configured or sized and shaped to couple to the cup 310 and the second end 354 may be configured or sized and shaped to couple to the stem 330. The adapter 350 may include a receiving portion 356 with at least one recess or groove 358 inset into the first end 352 of the adapter 350. The at least one groove 358 may be, for example, a circumferential groove inset into a portion of the adapter 350. The groove 358 may be, for example, designed or sized and shaped to mate with the at least one projection 322 extending from the lower portion or backside 318 of the stemless reverse cup 310. The adapter 350 may also include a joining member 360, for example, a male joining member or tongue 360 extending away from the second end 354 of the adapter 350. The joining member 360 may be configured or sized and shaped to fit into the joining member or at least one groove 338 in an upper end 332 of the stem 230. The joining member 360 may be, for example, a cylindrical projection 360 with a diameter that is tapered as it extends away from the second end 354 of the adapter 350. The tapered joining member 360 may be, for example, configured or sized and shaped to receive a similarly tapered opening 340 in the stem 330 by press fitting the adapter 350 and stem 330 together.

The adapter 350 may also be, for example, configured to achieve a desired offset or angle between the cup 310 and stem 330. For example, the joining member 360 may be positioned offset from a center point or central axis of the adapter 350. Further, the exterior size and shape of the adapter may provide the angulation of the cup 310 with respect to the stem 330. Alternatively or in addition to the adapter 350 providing the angulation, the joining member 360 may be positioned at an angle to the central axis of the adapter 350. It is also contemplated that the adapter 350 may be configured for angle customization and/or offset customization based on, for example, patient anatomy, humeral size, humeral diaphysis, and metaphysis offset.

Referring now to FIGS. 13-30, another reverse humeral implant 400 is shown. The reverse humeral implant 400 may include a stemless reverse cup 410, a stem 440, an adapter 460 for coupling the cup 410 and the stem 440, and an articulating cup liner 480. The terms "stemless reverse cup," "proximal reverse cup," "proximal cup," "proximal cup portion," "proximal cup component" and "cup" may be used interchangeably herein as they each refer to the portion of a shoulder implant that engages the glenoid or glenoid replacement. The terms "stem," "distal stem," "distal stem portion," "stem portion," "distal stem component," "stem component" may be used interchangeably herein as they each refer to the portion of the shoulder implant that is inserted into at least a portion of the humeral canal.

Figure 17:
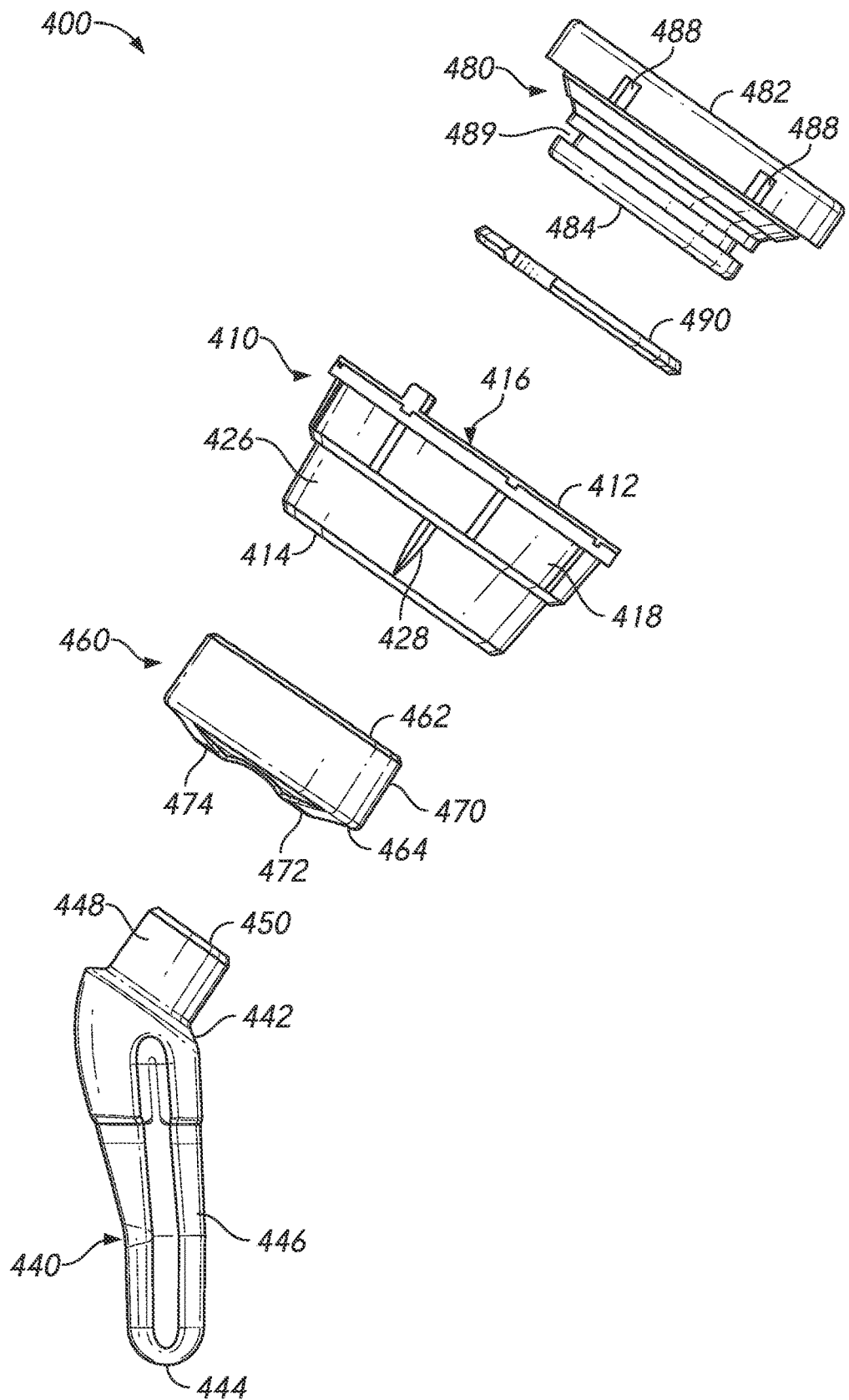
FIG. 17 is an exploded side view of the implant of FIG. 13, in accordance with an aspect of the present invention.
Figure 18:
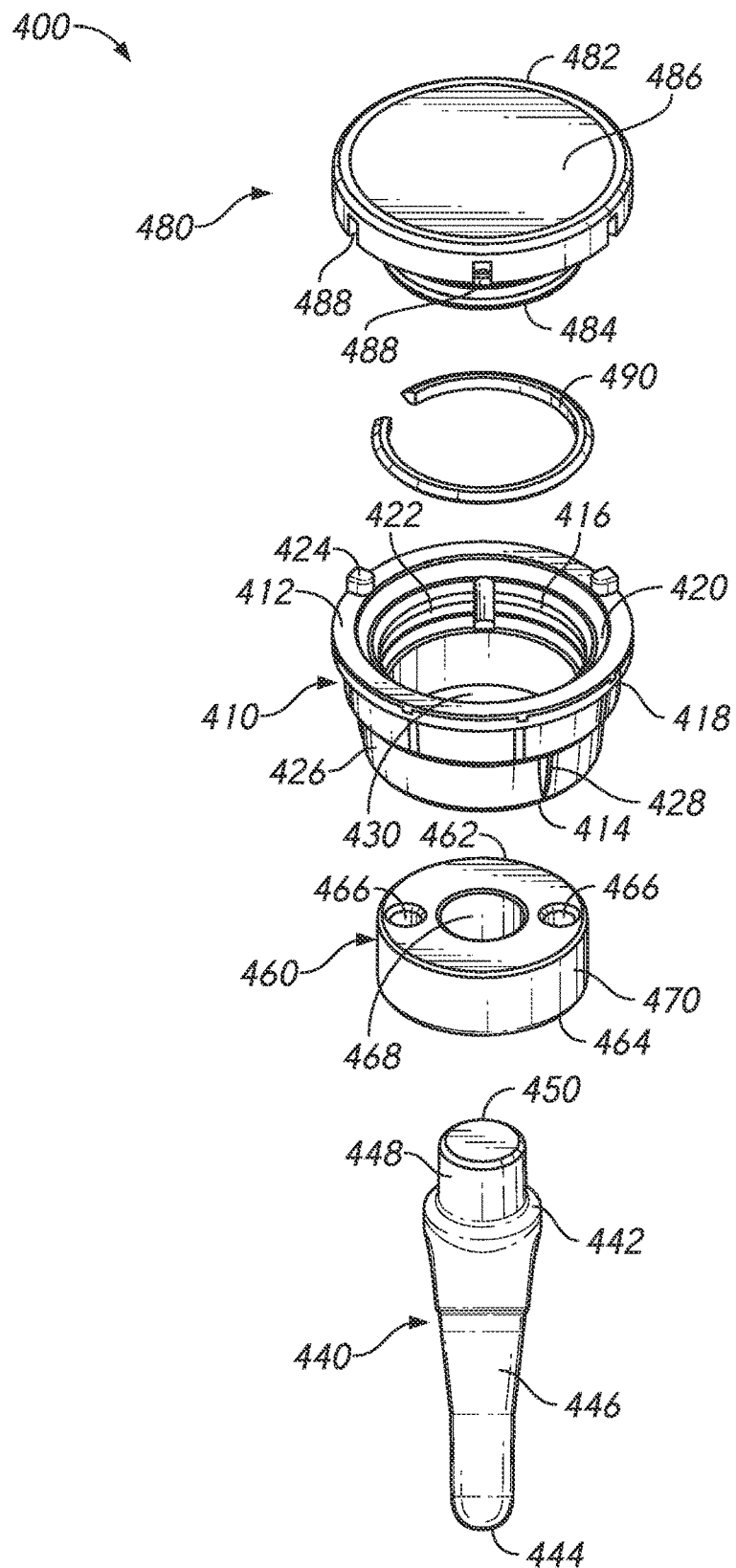
FIG. 18 is an exploded front view of the implant of FIG. 13, in accordance with an aspect of the present invention.
Figure 19:
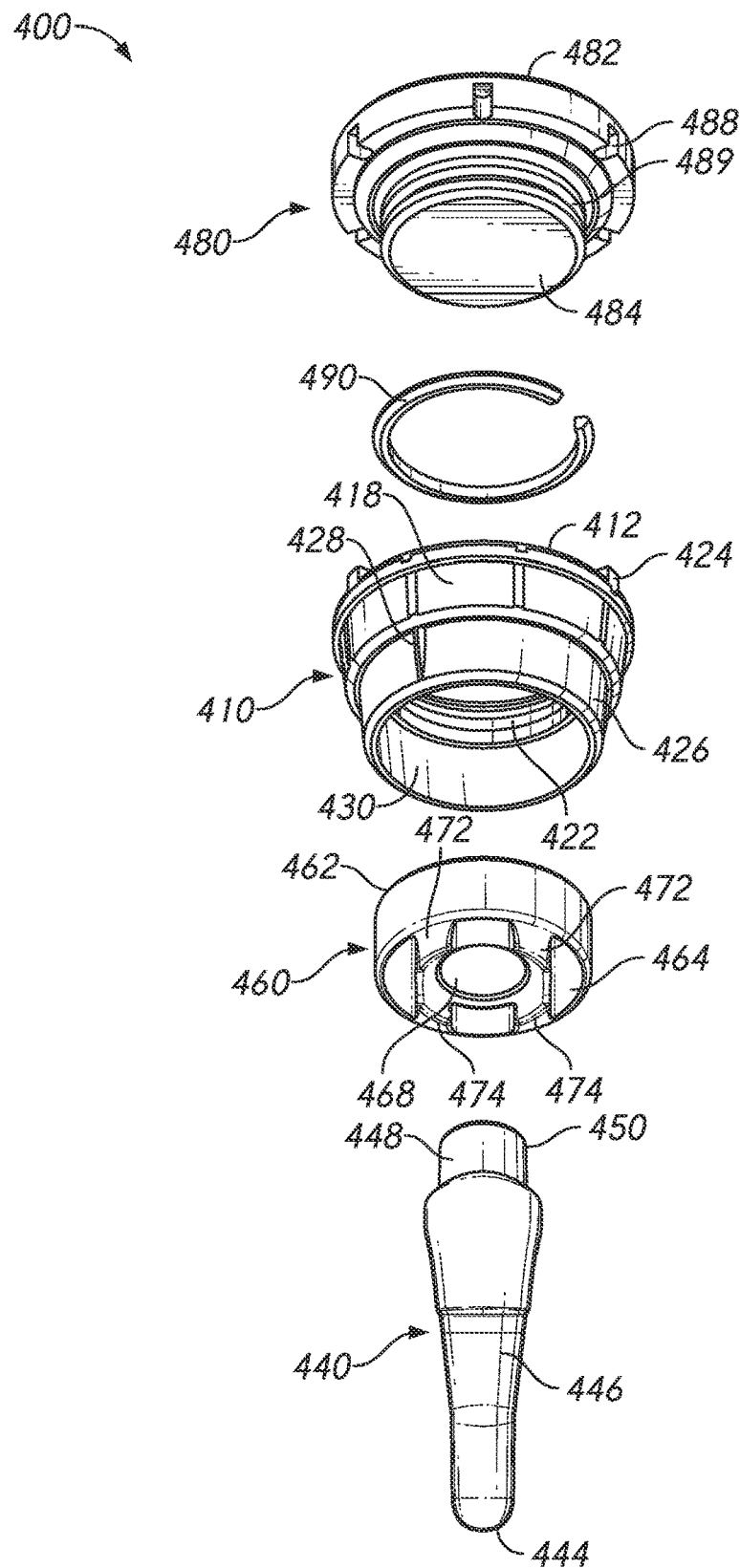
FIG. 19 is an exploded back view of the implant of FIG. 13, in accordance with an aspect of the present invention.
Figure 20:
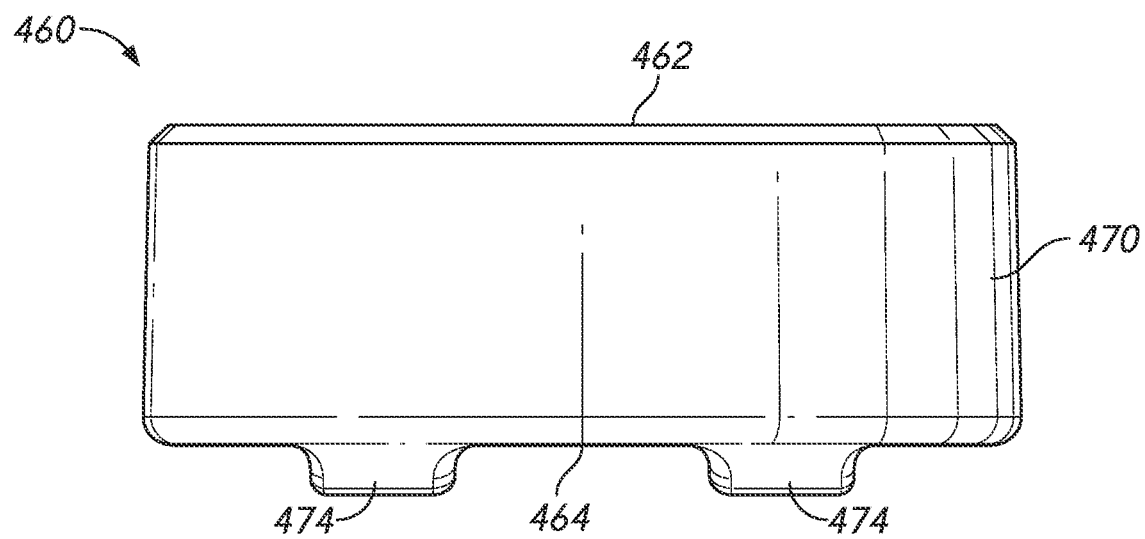
FIG. 20 is a front view of an adapter of the implant of FIG. 13, in accordance with an aspect of the present invention.
Figure 21:
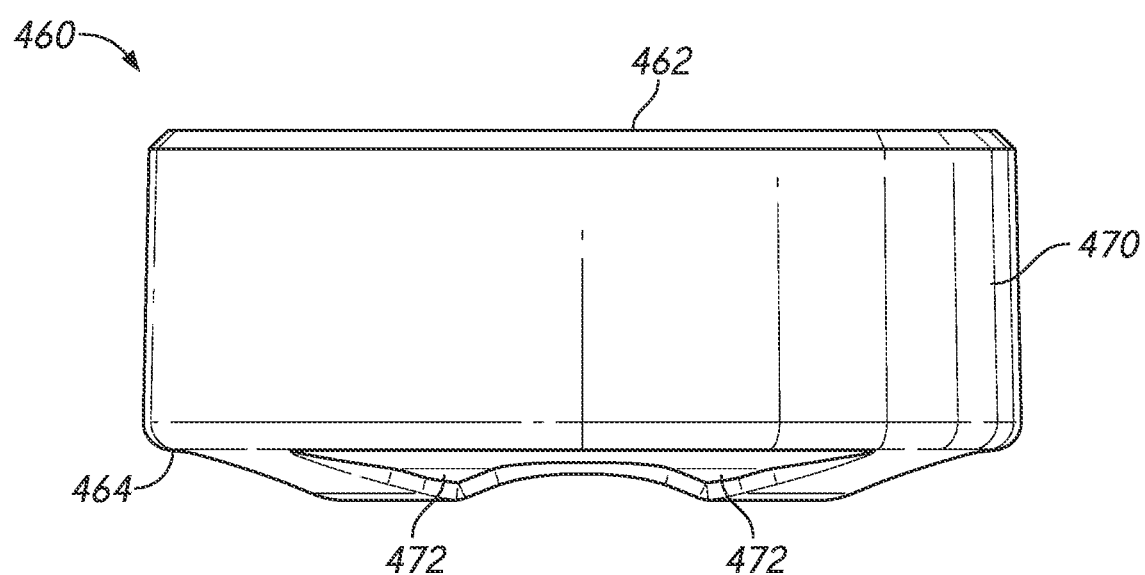
FIG. 21 is a side view of the adapter of FIG. 20, in accordance with an aspect of the present invention.

As shown in FIGS. 17-19, the cup 410 may include a first end 412 and a second end 414. The cup 410 may also include a recess or interior surface 416 and a backside, exterior surface or outer surface 418. The interior surface 416 may be positioned at and extend into the first end 412 of the cup 410. The interior surface 416 may be configured or sized and shaped to receive an articulating liner 480 which can receive a convex head attached to the glenoid region of the scapula. The backside 418 may extend from the first end 412 to the second end 414 on the exterior of the cup 410 and may be configured or sized and shaped to be received within the head of a humerus. The cup 410 may include an upper interior surface 420 with a recess 422 extending into the cup 410 for receiving a snap ring 490. The recess 422 may be configured or sized and shaped to receive and securely hold, for example, a liner 480 made of polyethylene or another material as known by one of skill in the art. The liner 480 may be configured or sized and shaped to snap fit into the recess 422. The liner 480 may also have a concave articular surface 486 to allow for the liner 480 to articulate with a convex head attached to, for example, the glenoid part of the scapula. The cup 410 may also include at least one protrusion 424 extending away from the first end 412 of the cup 410. The at least one protrusion 424 aligns with and engages a corresponding recess 488 in the liner 480. The cup 410 may also include, for example, a base portion 426 with at least one fin, rib, or projection 428 extending away from the base portion 426. The ribs 428 may include a surface or rib-like structure projecting from the base portion 426 of the reverse cup 410. The ribs 428 may project from the surface of the base portion 426 in, for example, a generally perpendicular orientation. The ribs 428 may also be configured or sized and shaped to provide rotational control under a torsional load, i.e., resist or prevent twisting or turning of the reverse cup 410 within the implant site after implantation. The stemless reverse cup 410 may optionally be made of a metallic material, such as for example, stainless steel, cobalt-chromium, titanium alloy, or any other like material as known by one of ordinary skill in the art. It is also contemplated that the stemless reverse cup 410 may include a metallic and/or biological porous coating to enhance bony integration. The biological porous coating may be, for example, pure HA, pure TCP, or a mix of HA/TCP.

The stem 440 may have a first end 442 and a second end 444. The stem 440 may include a base portion 446 extending from the second end 444 toward the first end 442 and a joining member 448 at the first end 442. The joining member 448 may be, for example, a male joining member 448, as shown in FIGS. 17-19. The joining member 448 may include an outer diameter 450, for example, smaller than the outer diameter of the base portion 446. The outer diameter 450 of the joining member 448 may, for example, taper as it extends away from the base portion 446.

Figure 22:
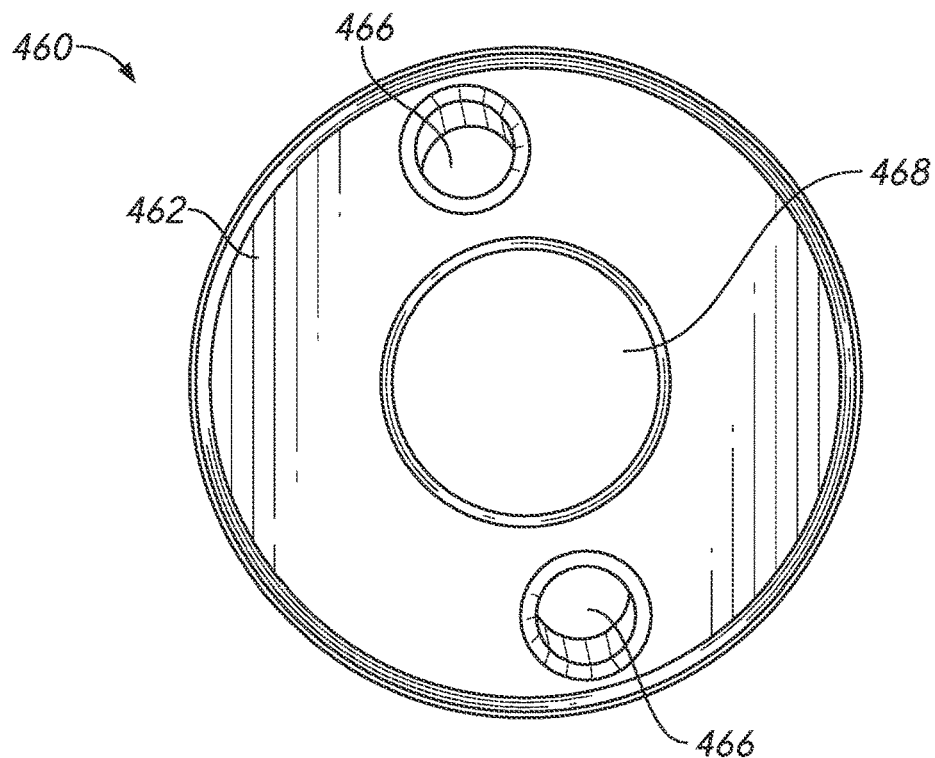
FIG. 22 is a top view of the adapter of FIG. 20, in accordance with an aspect of the present invention.
Figure 23:
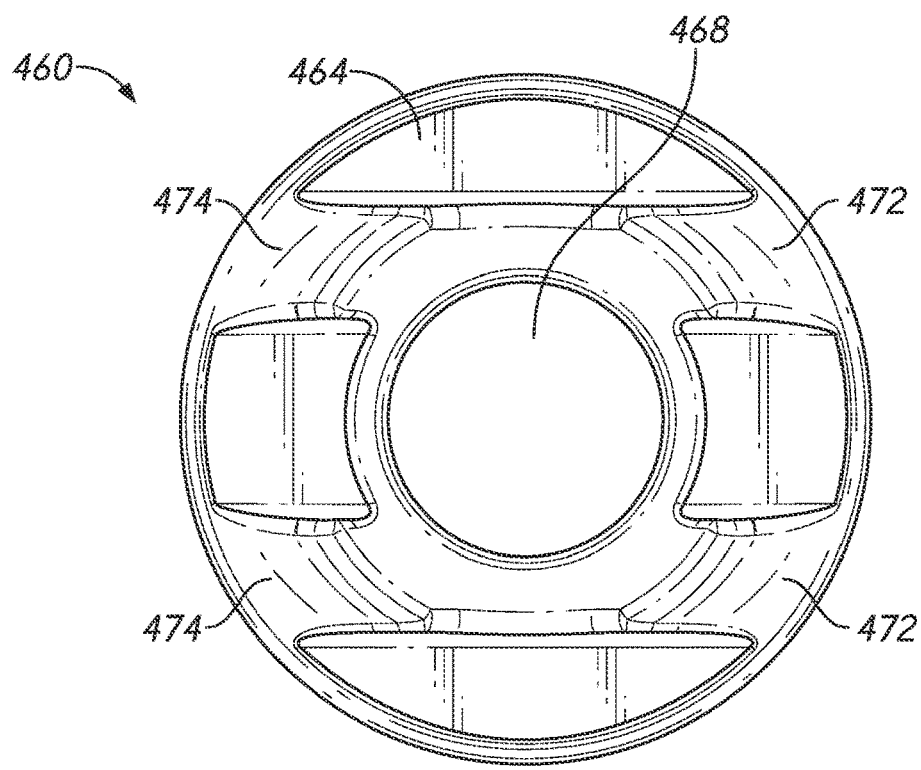
FIG. 23 is a bottom view of the adapter of FIG. 20, in accordance with an aspect of the present invention.
Figure 24:
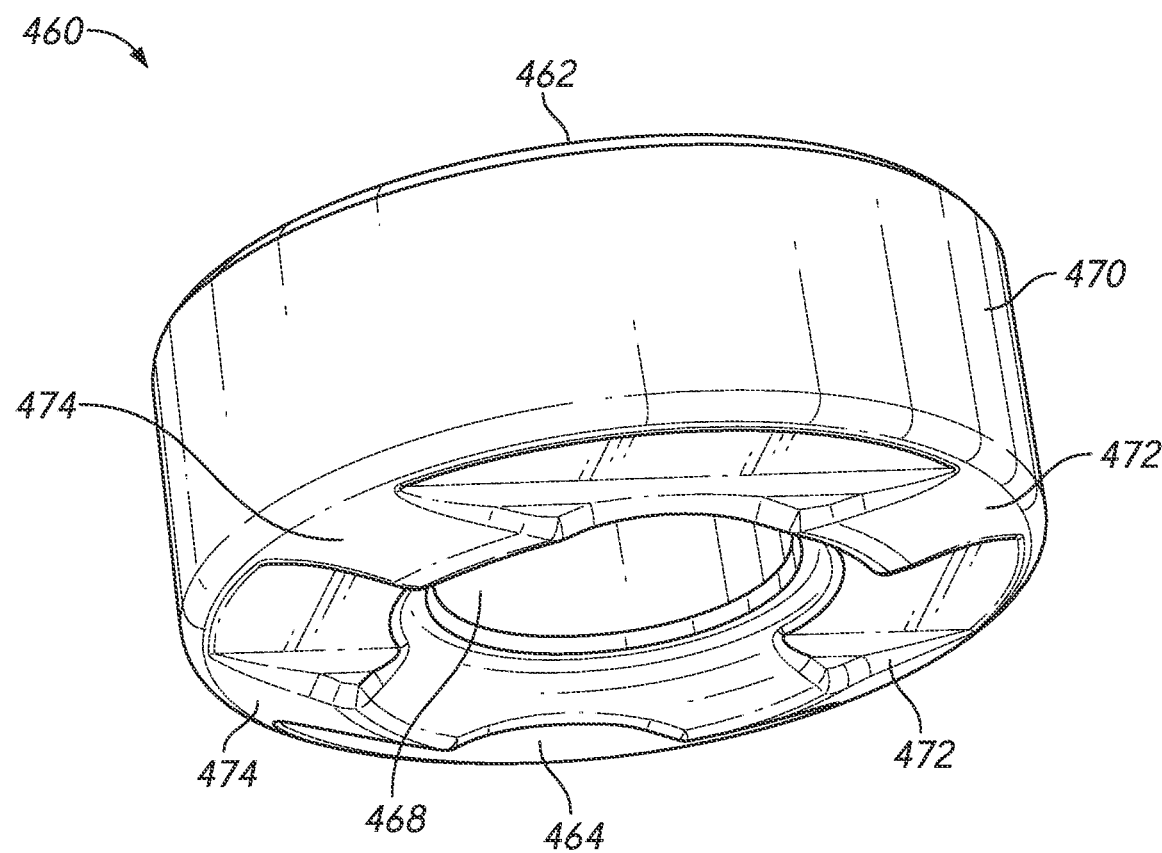
FIG. 24 is a bottom perspective view of the adapter of FIG. 20, in accordance with an aspect of the present invention.
Figure 25:
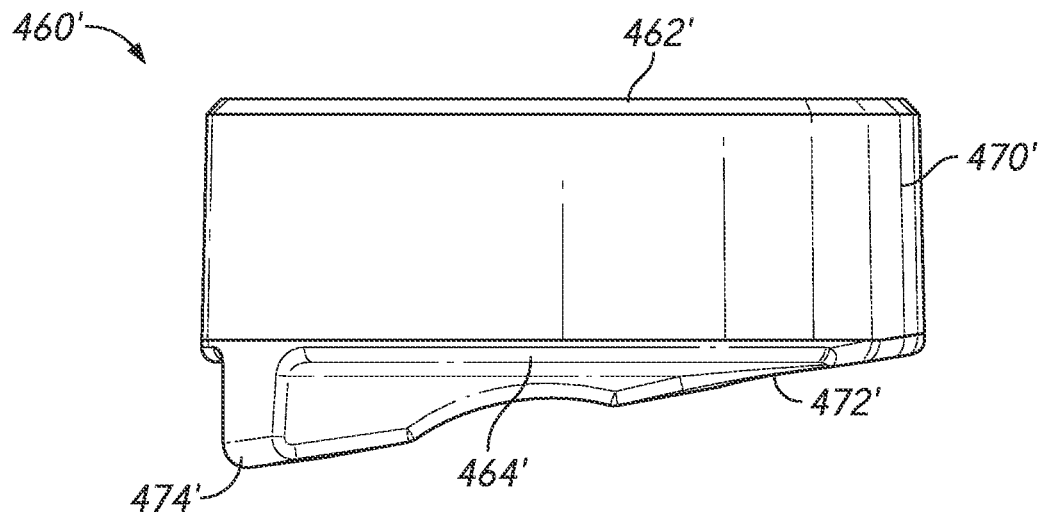
FIG. 25 is a side view of another adapter of the implant of FIG. 13, in accordance with an aspect of the present invention.
Figure 26:
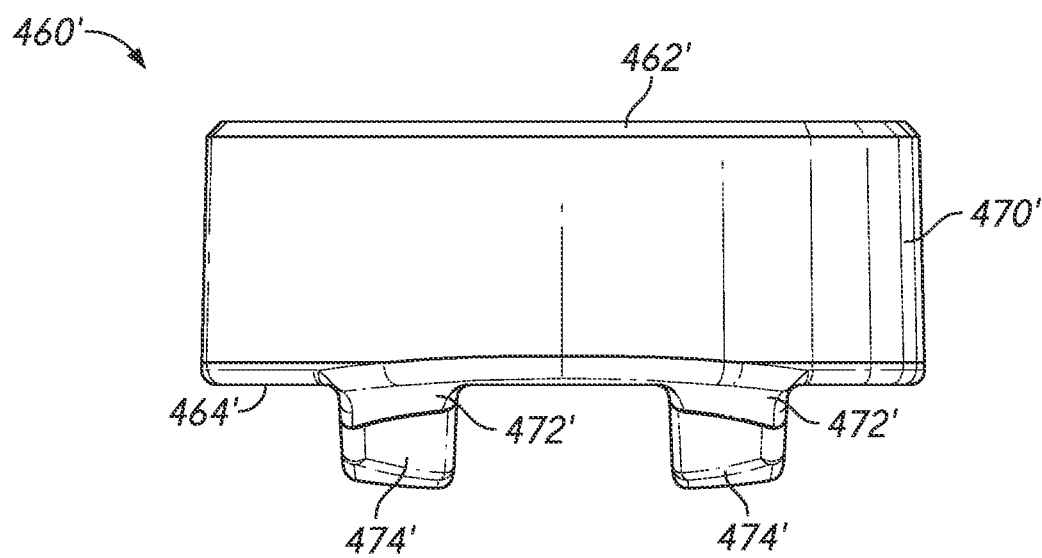
FIG. 26 is a back view of the adapter of FIG. 25, in accordance with an aspect of the present invention.
Figure 27:
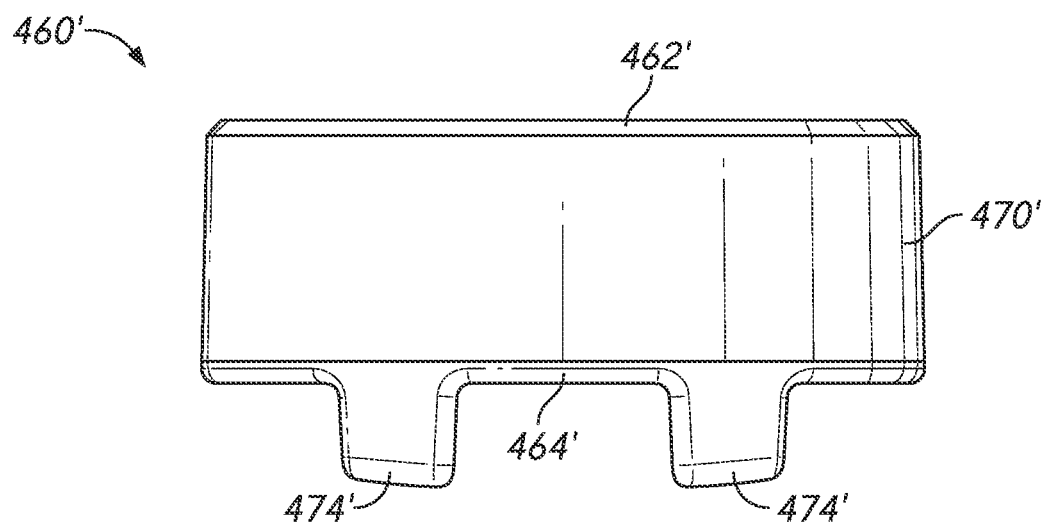
FIG. 27 is a front view of the adapter of FIG. 25, in accordance with an aspect of the present invention.
Figure 28:
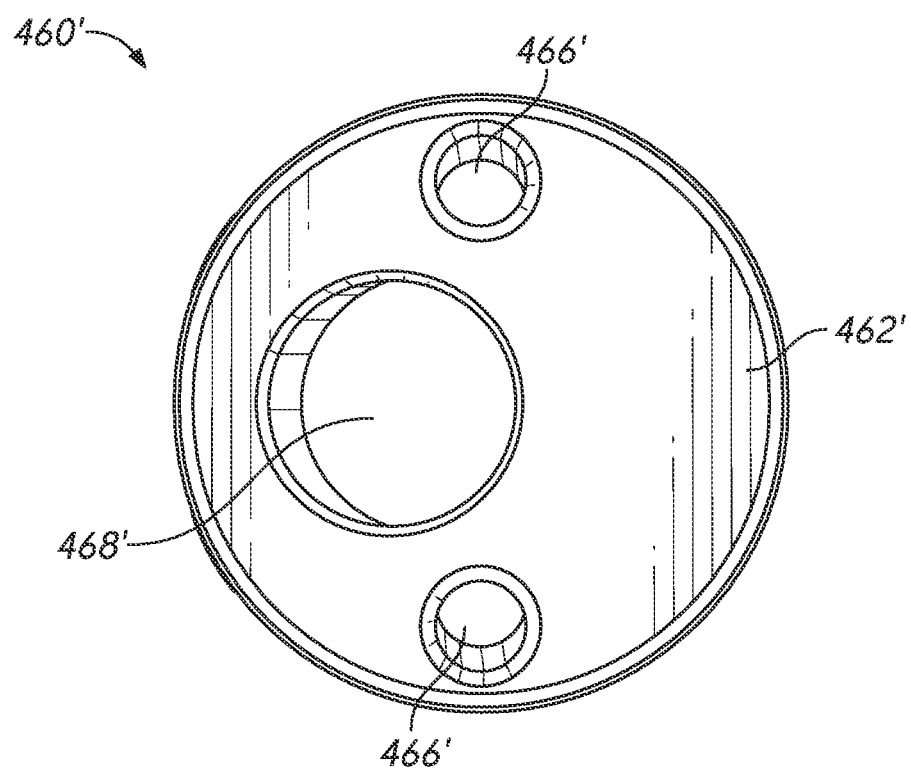
FIG. 28 is a top view of the adapter of FIG. 25, in accordance with an aspect of the present invention.
Figure 29:
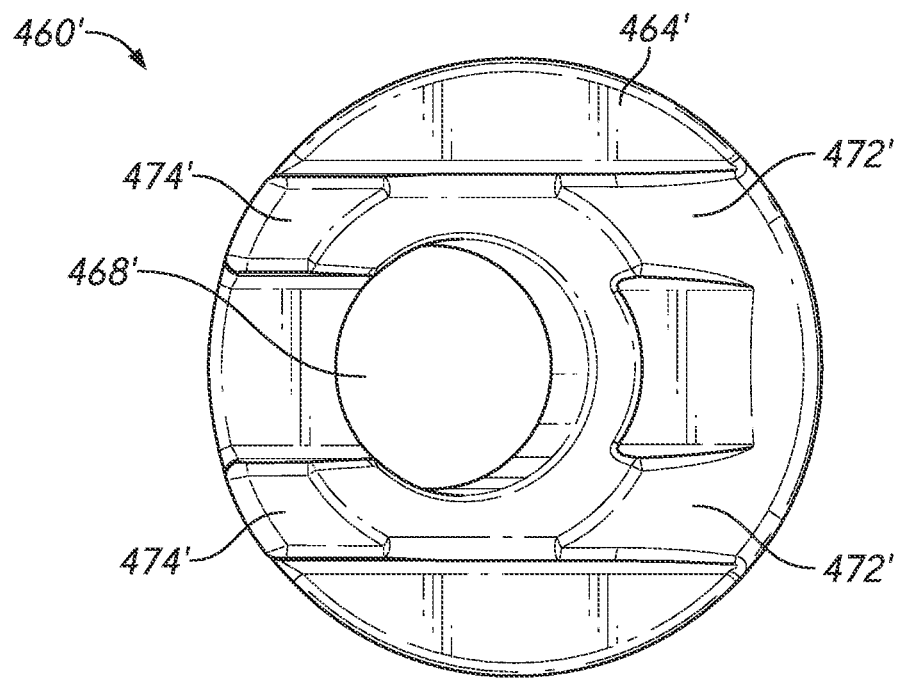
FIG. 29 is a bottom view of the adapter of FIG. 25, in accordance with an aspect of the present invention.
Figure 30:
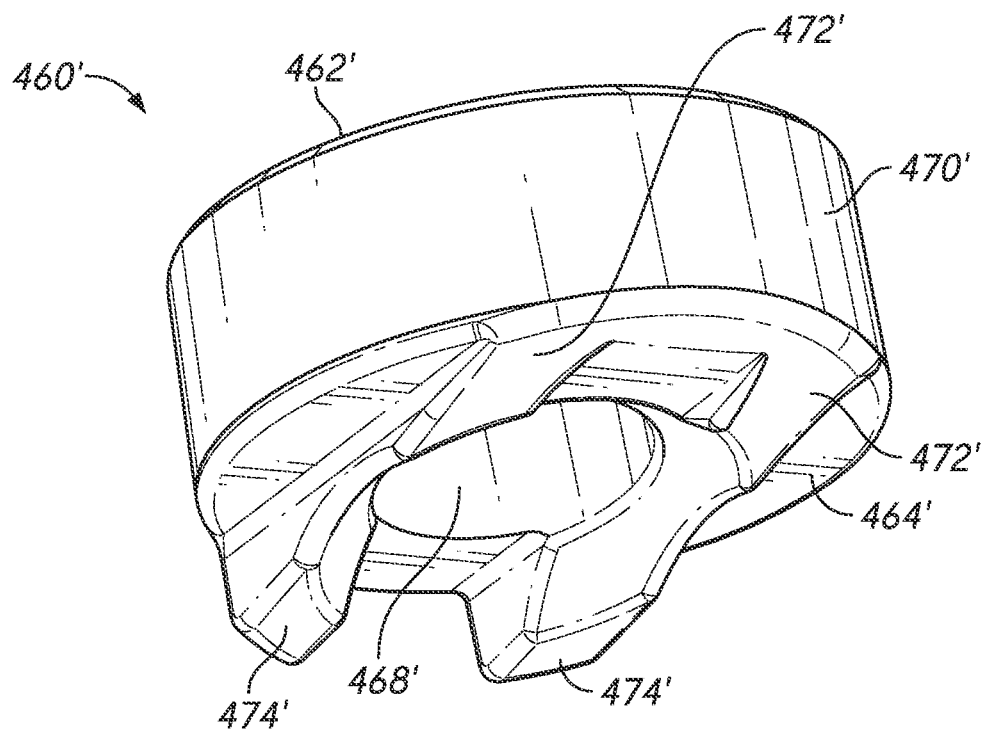
FIG. 30 is a bottom perspective view of the adapter of FIG. 25, in accordance with an aspect of the present invention.

With continued reference to FIGS. 17-19 and reference to FIGS. 20-30, the adapter 460 may have a first end 462 and a second end 464. The first end 462 may be configured or sized and shaped to couple to the cup 410 and the second end 464 may be configured or sized and shaped to couple to the stem 440. The adapter 460 may include at least one hole 466 inset into the first end 462 of the adapter 460. The at least one hole 466 may be, for example, designed or sized and shaped to secure the cup 410 to the adapter 460. The adapter 460 may also include an opening 468 extending into at least a portion of the adapter 460 from the second end 464. As shown in FIGS. 17-19, the opening 468 may pass through the entire length of the adapter 460. The opening 468 may be configured or sized and shaped to receive the joining member 448 of the stem 440. The opening 468 may be, for example, a cylindrical opening with a diameter that is tapered. The tapered opening 468 may be, for example, configured or sized and shaped to receive a similarly tapered joining member 448 of the stem 440 by press fitting the adapter 460 and stem 440 together. The opening 468 may extend through the adapter 460, for example, along the central axis of the adapter 460, as shown in FIGS. 22-24, or alternatively, the opening 468 may be offset from the center point or central axis of the adapter 460, such as shown in FIGS. 28-30. The position of the opening 468 may be selected to achieve a desired offset between the cup 410 and stem 440, along a longitudinal axis of the joining member 448 of the stem 440.

As shown in FIGS. 19, 23-24, and 29-30, the adapter 460, 460' may include a first set of feet, protrusions, or projections 472, 472' and a second set of feet, protrusions, or projections 474, 474'. As shown in FIGS. 20-24, each of the feet 472, 474 may, for example, have the same width and extend away from the second end 464 of the adapter 460 the same distance. Alternatively, as shown in FIGS. 25-30, the first feet 472' may, for example, have a first width and extend away from the second end 464' a first distance and the second feet 474' may, for example, have a second width and extend away from the second end 464' a second distance. The first distance may be, for example, smaller than the second distance. The first width may be smaller than the second width. The varying width of the first feet 472' compared to the second feet 474' allows for the adapter to provide angulation of the cup 410 with respect to a longitudinal axis of the joining member 448 of the stem 440. It is also contemplated that the adapter 460 may be configured for angle customization and/or offset customization based on, for example, patient anatomy, humeral size, humeral diaphysis, and metaphysis offset.

As shown in FIGS. 17-19, the articulating cup liner 480 may include a first end 482 and a second end 484. The liner 480 may include an articulating surface 486 at the first end 482. In addition, the liner 480 may include grooves 488 around the exterior surface of the liner 480 at the first end 482 and the grooves 488 may open toward the second end 484. The grooves 488 may be sized and shaped to receive the protrusions 424 on the cup 410 to assist with aligning and coupling the liner 480 to the cup 410. The liner 480 may further include a groove or recess 489 extending around a portion of the liner 480 near the second end 484 for receiving a snap ring 490, as shown in FIGS. 17 and 19. A portion of the snap ring 490 may be inserted into the groove 489 in the liner 480 and a portion of the snap ring 490 may fit into the recess 422 in the cup 410 to secure the liner 480 to the cup 410.

Referring now to FIGS. 1-30, one or more of the components of the prosthetic devices and systems 100, 200, 300, 400 disclosed herein can be customized or patient specific. For example, the below methods, analyses and optimizations, including associated computer readable medium and 3D printing devices, can be used to develop and create patient specific shoulder implant devices 100, 200, 300, 400, including the disclosed prosthetic including an inlay stemless reverse cup 110, 210, 310, 410, a stem 140, 230, 330, 440, and an intermediate dual taper adapter 160, 250, 350, 460.

In some aspects, a patient specific or customized intermediate dual taper adapter 160, 250, 350, 460 may include a desired angle and/or offset based on the methods of analysis and optimization disclosed herein. By way of example and not limitation, the angle and/or offset of the stem 140, 230, 330, 440 when connected to the cup 110, 210, 310, 410 by way of the adapter 160, 250, 350, 460 may be calculated based on an analysis of a patient's humeral diaphysis and metaphysis offset, among other things, using one or more pre-operative planning approaches disclosed herein.

The components of a humeral implant 100, 200, 300, 400 including, for example, a cup 110, 210, 310, 410, an adapter 160, 250, 350, 460 and a stem 140, 230, 330, 640 may be customized based on pre-operative planning. At least one of the cup 110, 210, 310, 410, the adapter 160, 250, 350, 460, and the stem 140, 230, 330, 440 may be customized. If only some of the components are customized, then, the remaining components may be at least one of "off-the-shelf" and standardized. For example, the cup 110, 210, 310, 410 and stem 140, 230, 330, 430 may be standardized, or come in an array of standardized shapes and sizes for selection as appropriate to the patient, while the adapter 160, 250, 350, 460 can be customized for each patient. The cups 110, 210, 310, 410, adapters 160, 250, 350, 460, and stems 140, 230, 330, 430 whether customized or standardized may be, for example, 3D printed.

Pre-operative planning methods and systems are also provided for selecting and/or designing a shoulder implant, including for example the prosthetic devices 100, 200, 300, 400 and systems disclosed herein. Such pre-operative planning may in some aspects take into consideration a plurality of factors and assessments, including, for example, one or more of the following, the combination and order of which may vary:

1. aligning the posterior edge of the glenoid implant with the posterior edge of the glenoid bone;
2. adjusting the glenoid retroversion to be about 0 degrees (0°) to a maximum of about 10 degrees (100);
3. adjusting the augmentation of the glenoid implant or the total distance necessary in the latero-medial direction between the center of rotation of the glenoid implant and the spino-glenoid notch to achieve the operative plan;
4. adjusting the inclination of the glenoid implant;
5. evaluating the back-side bone support for the glenoid implant, or the amount of the backside surface of the glenoid implant which is supported by or touching bone;
6. adjusting the medialization of the glenoid implant, or the volumetric amount of bone removed by reaming in order to shape the bone to match the operative plan, or the minimum total distance of reaming necessary in the medial direction to achieve the operative plan;
7. analyzing the fixation support;
8. analyzing the joint line, including comparing the pre-morbid joint line and the pathologic joint line and the new joint line, with the new joint line being as similar to a joint line defined based on several factors including the difference between the premorbid joint line and the pathologic joint line;
9. measuring and matching widths of the glenoid implant and the glenoid bone after reaming and aligning the inferior/superior axes of the glenoid implant and bone;
10. comparing vectors in three dimensions which represent the distance and direction between tendon and muscle insertions on the scapula and the humerus for measuring the distance of relocation of humeral tuberosity compared to the scapula;
11. determining the diameter of the humeral head, the height of humeral head, and location of humeral cut;
12. assessing the diameter of the humeral cut and determining the best size and location of humeral stemless cup from the internal size of the humeral bone with or without a factor applied according to Houndsfield unit measured by CT scan;
13. assessing the size and position of the diaphysis of the humeral shaft relative to the humeral metaphysis and selecting a modular stem size, shape, and an adapter from a range of adapters that will provide effective fixation of both the humeral cup and humeral stem;
14. determining the best fit size of implant from a range of sizes (length of stem, diameter of stem, diameter of stemless cup, height of stemless cup, height of humeral liner, diameter of humeral liner, offset and angle of adapter, diameter of adapter, height of adapter, radius of curvature of the articular surface);
15. conducting range of motion analysis, including virtually positioning implants through extreme ranges of motion to measure impact locations and compensate for necessary functional range of motion, wherein range of motion analysis can comprise optimization of adduction and/or abduction, elevation, flexion, extension, external and internal rotation range, and complex compound movements;
16. conducting soft tissue analysis, comprising determining key soft tissue insertion points, measuring distances in three dimensions for comparison to pre-operative conditions, and assessing lengths at extreme ranges of motion, such that total soft tissue length change or contraction is substantially maintained within anatomical ranges in order to substantially achieve most common activities of daily living;
17. assessing and adjusting as needed the thickness/height of the glenoid implant;
18. assessing and adjusting as needed the depth of the glenoid fossa;
19. assessing and adjusting as needed a graft, for example, graft thickness;
20. assessing and adjusting the size, shape and/or position of the stemless humeral cup;
21. assessing and adjusting the size, shape and/or position of the humeral stem and adapter; and/or
22. repeat steps 15 through 22 as necessary to achieve objectives.

In some embodiments, analyzing the joint line may include comparing the premorbid joint line, the pathologic joint line and the new joint line and analyzing the humeral lateralization. Humeral lateralization may be determined by the distance the humeral shaft is moved laterally relative to the scapula after the implants are placed.

In some embodiments, the above method of creating a shoulder surgery guide based on pre-operative planning may further include one or more of the below optimization limitations. Such optimization limitation may include, for example, the identification of procedural risks based on measurements of whether: the glenoid face coverage is maximized; the overhang of the glenoid face is minimized; the bone removal on the glenoid face is minimized, such as for example less than about 2 mm of depth; the glenoid retroversion is less than about 5 degrees; the "seating" of the glenoid implant is greater than about 80%, i.e. about 80% of the back side of the glenoid implant is supported by or touching bone; the depth of any glenoid implant augment feature is as minimal as possible; there is less than about 1 mm of difference between the premorbid or the pathologic joint line and the new joint line with implants; there is minimized penetration of the glenoid cortical wall medially; there is maximized bone thickness behind glenoid, preferably greater than 3 mm; the orientation offset between the native glenoid and implant superior/inferior axis is minimized, preferably less than 5 degrees; the superior or inferior tilt versus anatomy is minimized, preferably less than 5 degrees; there is less than about 5% change in soft tissue length at extreme ranges of motion; there is an absence of a humeral cortical wall penetration by any portion of the humeral implant; there is minimal difference in diameter in the cut plane between the humeral stemless cup and the internal diameter of the humeral cortical wall, for example, less than 3 mm; there is greater tuberosity to medial head edge comparison to bony anatomy, in some embodiments less than 2 mm; the bone removal on the humeral face is minimized, such as for example, less than about two-thirds of the humeral head thickness; the seating of the stemless cup is greater than about 80%, i.e., about 80% of the backside of the stemless cup is supported by or touching bone; there is maximized bone thickness behind the stemless cup, preferably greater than 3 mm; there is minimized translation offset in the cut plane between the projection of the native humeral center of rotation and the center of rotation of the implant, preferably less than 2 mm; there is a height offset in the range of about 15 mm to about 25 mm between the native humeral center of rotation and the center of rotation of the implant to ensure adequate lengthening of the arm; there is minimized offset and tilt between the bony diaphyseal humeral axis and the stem axis, preferably, less than 2 mm and/or 5 degrees (5°); and there is maximized filling of the humeral shaft while still ensuring no implant contact with the cortical wall of the humeral shaft, for example, the filling may be in the range of 50% to 90% of intramedullary bone filled based on an identification of intramedullary bone by use of Houndsfield units.

The above method may further include recommending implants and placement positions, with recommended adjustments in glenoid implant size, augmentation depth, augment position, positioning in six degrees of freedom, fixation type, fixation size, reaming depth, reaming diameter, and reaming angle(s), seating ratio, wherein the reaming angles may include retroversion and inclination. The above method may further include recommending implants and placement positions, with recommended adjustments in humerus stem size, length, head diameter, head height, head offset, rotation (axial), humeral diaphysis and metaphysis offset.

The method of creating a patient specific adapter for the disclosed humeral implant includes: utilizing one or more of the above limitations, analyses, optimizations and recommendations to create an adaptable humeral offset prosthesis. Such prosthetic creation may include automated design and creation of a three dimensional model of a glenoid and/or humeral guide reflecting one or more optimized parameters determined during pre-operative planning based on the above described method.

The subject matter described herein may be implemented in software in combination with hardware and/or firmware. For example, the subject matter described herein may be implemented in software executed by a processor. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory devices, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

As used herein, the term "node" refers to a physical computing platform including one or more processors and memory.

As used herein, the terms "function" or "module" refer to hardware, firmware, or software in combination with hardware and/or firmware for implementing features described herein.

In some embodiments, a computer readable medium is provided, having stored thereon executable instructions that when executed by the processor of a computer, control the computer to perform steps including generating a virtual three dimensional model of a glenoid and/or humeral guide reflecting one or more optimized parameters determined during pre-operative planning based on the above described method. In some embodiments, a computer readable medium is provided, having stored thereon executable instructions that when executed by the processor of a computer control a 3D printing device in communication with the computer, whereby the 3D printing device prints a humeral prosthesis or component thereof, e.g. adapter, for use in shoulder replacement surgery in a patient for which the optimization analysis was conducted.

In some embodiments, methods of treating a patient, and/or surgical methods, are provided, wherein one or more of the disclosed methods of analysis and optimization are performed on a patient in need of shoulder or other joint surgery. The methods of treating a patient may include performing analysis and optimization, designing and creating an optimized prosthesis, or selecting from an array. The method of treating a patient may also include utilizing the pre-operative planning to design and optimize one or more glenoid and/or humeral implants and surgically implanting the one or more glenoid and/or humeral prosthetic devices.

A kit may also be provided, wherein the kit may include a set of instructions for performing the disclosed pre-operative planning methods and analyses. Such a kit may further include one or more glenoid and/or humeral prosthetic devices, wherein the devices are customizable or modular in design such that the prosthetic device can be optimized for the patient based on the pre-operative planning analysis. In some embodiments, the kit may further have a guide for placing a prosthetic device during shoulder surgery, wherein the guide can be optimized for the patient based on the pre-operative planning analysis. The kit may also use a 3-D printing device for producing a guide and/or one or more glenoid and/or humeral prosthetic devices. Further, the kit may include a computer-readable medium (software) for use in conducting the pre-operative planning, and designing a guide, glenoid implant and/or humeral implant based on input parameters gathered during the disclosed methods of analysis.

It is contemplated that the patient may be a mammalian subject. For example, the patient may be a human subject, including an adult, adolescent or child.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

The invention claimed is:

1. A pre-operative planning method for designing a humeral prosthetic implant having a cup including a stem projecting outwardly from a surface of the cup at at least one of an offset and an angle, the method comprising:
analyzing one or more of humerus stem size, length, head diameter, head height, head offset, rotation (axial), humeral diaphysis and/or metaphysis offset of a patient to be treated,
wherein the cup includes:
a first end and a second end, the first end defining a first interior recess that extends inwardly toward the second end;
an exterior backside extending from the second end toward the first end;
wherein a second additional recess is defined at the first end of the cup, the second additional recess sized and configured to receive a snap ring when the snap ring is inserted into a groove in an articular liner such that the interior recess is configured to receive and securely hold the articular liner, and
wherein the exterior backside is configured to be received within the head of the humerus, the exterior backside including at least one fin, rib, or projection extending away from the exterior backside and which is configured or sized and shaped to provide rotational control under a torsional load; and
storing a design for the humeral prosthetic implant in a non-transitory computer readable media.

2. The method of claim 1, further comprising:
designing the humeral prosthetic implant based upon one or more anatomic measurements.

3. The method of claim 1, further comprising producing the humeral prosthetic implant based upon the design for the humeral prosthetic implant.

4. The method of claim 3, wherein producing the humeral prosthetic implant comprises using a 3D printing device.

5. The pre-operative planning method of claim 1, wherein the at least one fin, rib, or projection comprises ribs that projects from a surface of a base portion of the cup in a generally perpendicular orientation.

6. The pre-operative planning method of claim 1, wherein the humeral prosthetic implant further comprises a biological porous coating to enhance bony integration.

7. The pre-operative planning method of claim 1, further comprising forming the cup through additive manufacturing.

8. The pre-operative planning method of claim 1, wherein the humeral prosthetic implant further comprises at least one protrusion extending away from the first end of the cup, the at least one protrusion configured to align with and engage a corresponding recess in an articulating liner received into the interior recess.

9. The pre-operative planning method of claim 1, wherein the exterior backside includes an opening configured to receive an adapter.

10. The pre-operative planning method of claim 9, wherein the opening has an inner wall with a tapered diameter.

11. The pre-operative planning method of claim 1, wherein the humeral prosthetic implant further comprises an articulating liner, wherein the articulating liner is configured to snap-fit into the interior recess.

12. The pre-operative planning method of claim 11, wherein the articulating liner has a concave articular surface to allow for the articulating liner to articulate with a convex head attached, in use, to a glenoid part of a scapula.

13. The pre-operative planning method of claim 1, wherein the articulating liner defines a plurality grooves, each groove of the plurality of grooves defined by the articulating liner is sized and shaped to receive at least one protrusion to assist with aligning and coupling the articulating liner to the cup portion.

* * * * *